(12) United States Patent
Gordon et al.

(10) Patent No.: US 7,316,714 B2
(45) Date of Patent: Jan. 8, 2008

(54) ARTIFICIAL FUNCTIONAL SPINAL UNIT ASSEMBLIES

(75) Inventors: Charles Gordon, Tyler, TX (US);
Corey Harbold, Tyler, TX (US)

(73) Assignee: Flexuspine, Inc., Tyler, TX (US)

( * ) Notice: Subject to any disclaimer, the term of this patent is extended or adjusted under 35 U.S.C. 154(b) by 38 days.

(21) Appl. No.: 10/660,155

(22) Filed: Sep. 11, 2003

(65) Prior Publication Data

US 2005/0033431 A1 Feb. 10, 2005

Related U.S. Application Data

(63) Continuation-in-part of application No. 10/634,950, filed on Aug. 5, 2003, now Pat. No. 7,204,853.

(51) Int. Cl.
*A61F 2/44* (2006.01)
*A01B 17/68* (2006.01)

(52) U.S. Cl. .............................. 623/17.16; 623/17.15; 606/61

(58) Field of Classification Search .. 623/17.11–17.16; 606/61
See application file for complete search history.

(56) References Cited

U.S. PATENT DOCUMENTS

| 4,611,581 A | 9/1986 | Steffee |
| 4,696,290 A | 9/1987 | Steffee |
| 4,854,311 A | 8/1989 | Steffee |
| 4,863,476 A | 9/1989 | Shepperd |
| 4,863,477 A | 9/1989 | Monson |
| 4,946,458 A | 8/1990 | Harms et al. |
| 5,042,982 A | 8/1991 | Harms et al. |
| 5,092,867 A | 3/1992 | Harms et al. |
| 5,192,326 A | 3/1993 | Bao et al. |

(Continued)

FOREIGN PATENT DOCUMENTS

WO 2004019762 3/2004

(Continued)

OTHER PUBLICATIONS

Invitation To Pay Additional Fees From the International Searching Authority for PCT/US2004/025090 mailed on Dec. 7, 2004 (8 pages).

(Continued)

*Primary Examiner*—David J. Isabella
(74) *Attorney, Agent, or Firm*—Meyertons, Hood, Kivlin, Kowert & Goetzel, P.C.; Eric B. Meyertons

(57) ABSTRACT

An artificial functional spinal unit is provided comprising, generally, an expandable artificial intervertebral implant that can be placed via a posterior surgical approach and used in conjunction with one or more artificial facet joints to provide an anatomically correct range of motion. Expandable artificial intervertebral implants in both lordotic and non-lordotic designs are disclosed, as well as lordotic and non-lordotic expandable cages for both PLIF (posterior lumber interbody fusion) and TLIF (transforaminal lumbar interbody fusion) procedures. The expandable implants may have various shapes, such as round, square, rectangular, banana-shaped, kidney-shaped, or other similar shapes. By virtue of their posteriorly implanted approach, the disclosed artificial FSU's allow for posterior decompression of the neural elements, reconstruction of all or part of the natural functional spinal unit, restoration and maintenance of lordosis, maintenance of motion, and restoration and maintenance of disc space height.

20 Claims, 19 Drawing Sheets

U.S. PATENT DOCUMENTS

| | | |
|---|---|---|
| 5,196,013 A | 3/1993 | Harms et al. |
| 5,207,678 A | 5/1993 | Harms et al. |
| 5,261,909 A | 11/1993 | Sutterlin et al. |
| 5,314,477 A | 5/1994 | Marnay |
| 5,443,467 A | 8/1995 | Biedermann et al. |
| 5,498,263 A | 3/1996 | DiNello et al. |
| 5,545,165 A | 8/1996 | Biedermann et al. |
| 5,672,176 A | 9/1997 | Biedermann et al. |
| 5,725,527 A | 3/1998 | Biedermann et al. |
| 5,782,832 A | 7/1998 | Larsen et al. |
| 5,810,819 A | 9/1998 | Errico et al. |
| 5,961,518 A | 10/1999 | Errico et al. |
| 5,997,539 A | 12/1999 | Errico et al. |
| 6,017,344 A | 1/2000 | Errico et al. |
| 6,045,579 A | 4/2000 | Hochschuler et al. |
| 6,063,089 A | 5/2000 | Errico et al. |
| RE36,758 E | 6/2000 | Fitz |
| 6,080,193 A | 6/2000 | Hochschuler et al. |
| 6,102,950 A | 8/2000 | Vaccaro |
| 6,106,526 A | 8/2000 | Harms et al. |
| 6,113,637 A | 9/2000 | Gill et al. |
| 6,132,464 A | 10/2000 | Martin |
| 6,217,579 B1 | 4/2001 | Koros |
| RE37,665 E | 4/2002 | Ralph et al. |
| 6,375,682 B1 | 4/2002 | Fleischmann et al. |
| 6,413,259 B1 | 7/2002 | Lyons et al. |
| 6,419,704 B1 | 7/2002 | Ferree |
| 6,443,990 B1 | 9/2002 | Aebi et al. |
| 6,447,544 B1 | 9/2002 | Michelson |
| 6,451,021 B1 | 9/2002 | Ralph et al. |
| 6,454,806 B1 | 9/2002 | Cohen et al. |
| 6,478,823 B1 | 11/2002 | Michelson |
| 6,482,207 B1 | 11/2002 | Errico |
| 6,500,205 B1 | 12/2002 | Michelson |
| 6,533,818 B1 | 3/2003 | Weber et al. |
| 6,540,748 B2 | 4/2003 | Lombardo |
| 6,558,423 B1 | 5/2003 | Michelson |
| 6,562,074 B2 | 5/2003 | Gerbec et al. |
| 6,565,605 B2 | 5/2003 | Goble et al. |
| 6,569,442 B2 | 5/2003 | Gan et al. |
| 6,576,016 B1 | 6/2003 | Hochschuler et al. |
| 6,579,318 B2 | 6/2003 | Varga et al. |
| 6,579,319 B2 | 6/2003 | Goble et al. |
| 6,582,467 B1 | 6/2003 | Teitelbaum et al. |
| 6,610,091 B1 | 8/2003 | Reiley |
| 6,616,671 B2 | 9/2003 | Landry et al. |
| 6,641,614 B1 | 11/2003 | Wagner et al. |
| 6,648,893 B2 | 11/2003 | Dudasik |
| 6,648,915 B2 | 11/2003 | Sazy |
| 6,648,917 B2 | 11/2003 | Gerbec et al. |
| 6,679,915 B1 | 1/2004 | Cauthen |
| 6,685,742 B1 | 2/2004 | Jackson |
| 6,706,070 B1 | 3/2004 | Wagner et al. |
| 6,811,567 B2 | 11/2004 | Reiley |
| 6,852,129 B2 | 2/2005 | Gerbec et al. |
| 6,863,673 B2 | 3/2005 | Gerbec et al. |
| 2001/0020476 A1 | 9/2001 | Gan et al. |
| 2002/0065557 A1 | 5/2002 | Goble et al. |
| 2002/0123806 A1 | 9/2002 | Reiley |
| 2002/0128659 A1 | 9/2002 | Michelson |
| 2003/0028250 A1 | 2/2003 | Reiley et al. |
| 2003/0069643 A1 | 4/2003 | Ralph et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0135275 A1 | 7/2003 | Garcia et al. |
| 2003/0139812 A1 | 7/2003 | Garcia et al. |
| 2003/0204259 A1 | 10/2003 | Goble et al. |
| 2003/0233145 A1 | 12/2003 | Landry et al. |
| 2004/0006391 A1 | 1/2004 | Reiley |
| 2004/0044411 A1 | 3/2004 | Suddaby |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049280 A1 | 3/2004 | Cauthen |
| 2004/0049281 A1 | 3/2004 | Reiley |
| 2004/0117020 A1 | 6/2004 | Frey et al. |
| 2004/0127989 A1 | 7/2004 | Dooris et al. |
| 2004/0167626 A1 | 8/2004 | Geremakis et al. |
| 2004/0254643 A1 | 12/2004 | Jackson |
| 2004/0254644 A1 | 12/2004 | Taylor |
| 2004/0267364 A1 | 12/2004 | Carli et al. |
| 2004/0267369 A1 | 12/2004 | Lyons et al. |
| 2005/0010295 A1 | 1/2005 | Michelson |
| 2005/0015146 A1 | 1/2005 | Louis et al. |
| 2005/0015149 A1 | 1/2005 | Michelson |
| 2005/0021144 A1 | 1/2005 | Malberg et al. |
| 2005/0033432 A1 | 2/2005 | Gordon et al. |
| 2005/0033439 A1 | 2/2005 | Gordon et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |

FOREIGN PATENT DOCUMENTS

| | | |
|---|---|---|
| WO | 2004019828 | 3/2004 |
| WO | 2004019829 | 3/2004 |
| WO | 2004019830 | 3/2004 |
| WO | 2004024011 | 3/2004 |

OTHER PUBLICATIONS

Claims from U.S. Appl. No. 11/050,632 to Gordon et al. entitled "Functional Spinal Units" filed Feb. 3, 2005.

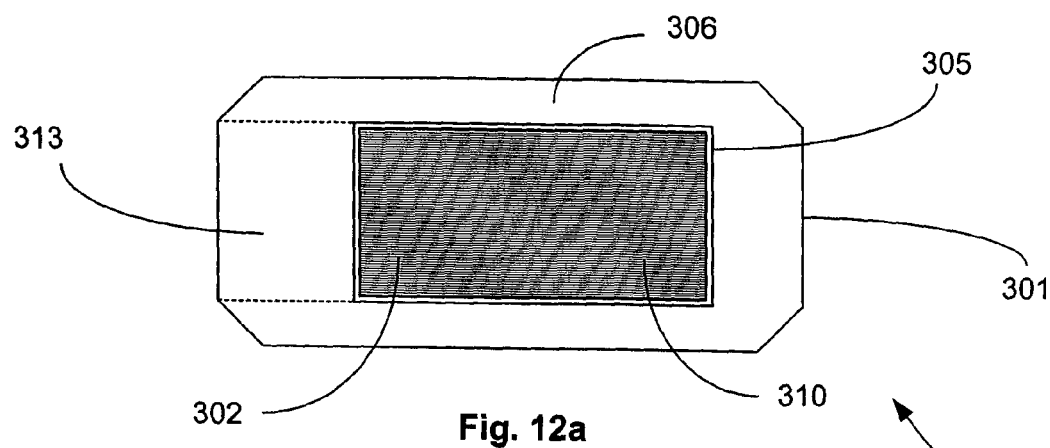
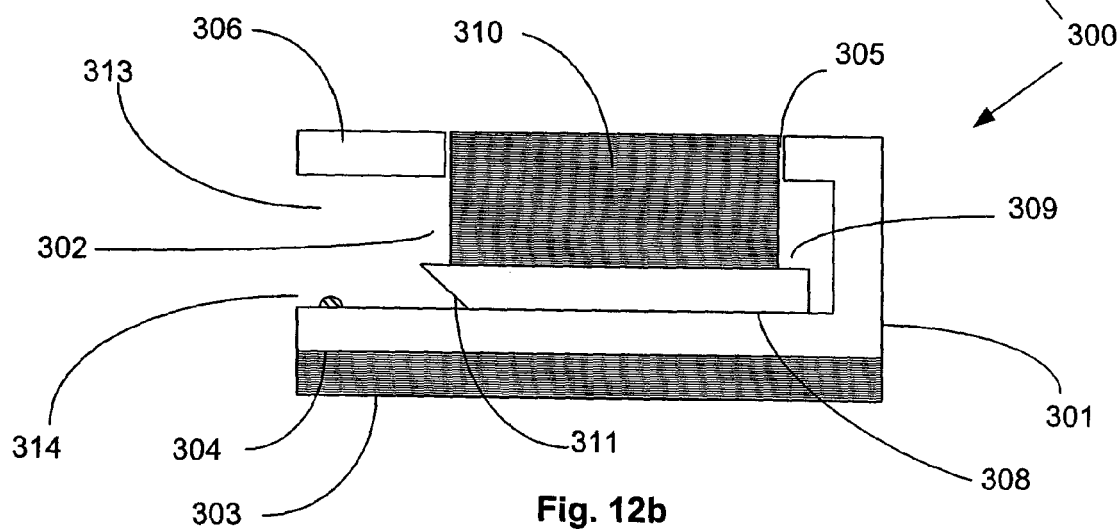
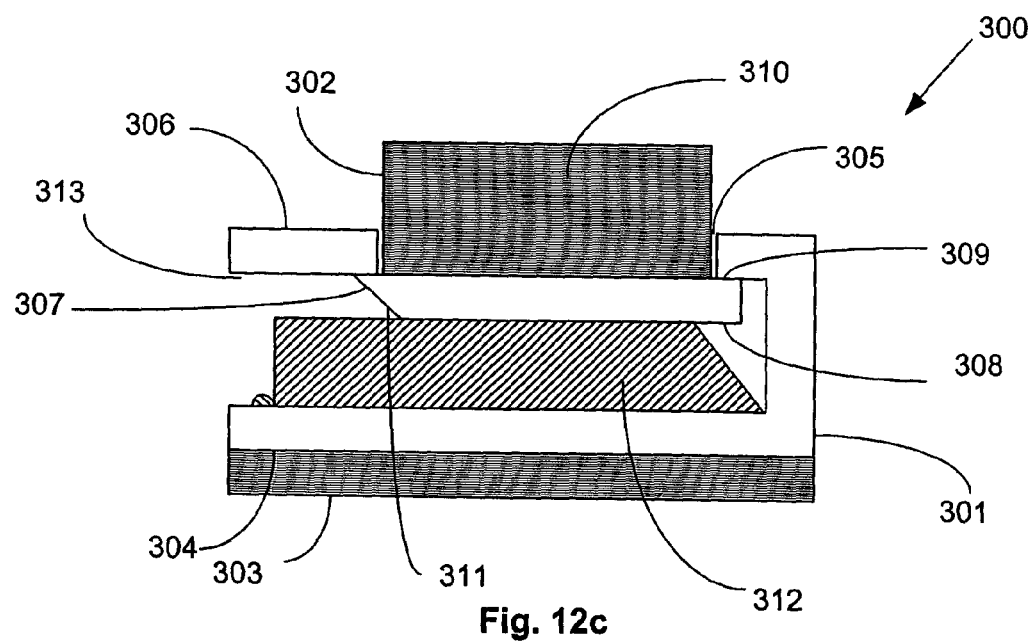

810   Fig. 17a   800

ARTIFICIAL FUNCTIONAL SPINAL UNIT ASSEMBLIES

This application is a continuation-in-part of U.S. patent application Ser. No. 10/634,950, filed Aug. 5, 2003 now U.S. Pat No. 7,204,853.

STATEMENT REGARDING FEDERALLY SPONSORED RESEARCH OR DEVELOPMENT

Not Applicable

FIELD OF THE INVENTION

The present invention generally relates to functional spinal implant assemblies for insertion into the intervertebral space between adjacent vertebral bones and reconstruction of the posterior elements to provide stability, flexibility and proper biomechanical motion. More specifically, the present invention relates to artificial functional spinal units comprising an expandable artificial intervertebral implant that can be inserted via a posterior surgical approach and used in conjunction with one or more artificial facet joints to provide a more anatomically correct range of motion.

BACKGROUND OF THE INVENTION

The human spine is a complex mechanical structure composed of alternating bony vertebrae and fibrocartilaginous discs that are connected by strong ligaments and supported by musculature that extends from the skull to the pelvis and provides axial support to the body. The intervertebral discs primarily serve as a mechanical cushion between adjacent vertebral segments of the spinal column and generally comprise three basic components: the nucleus pulposus, the anulus fibrosis, and two vertebral end plates. The end plates are made of thin cartilage overlying a thin layer of hard cortical bone that attaches to the spongy, cancellous bone of the vertebral body. The anulus fibrosis forms the disc's perimeter and is a tough outer ring that binds adjacent vertebrae together. The vertebrae generally comprise a vertebral foramen bounded by the anterior vertebral body and the neural arch, which consists of two pedicles and two laminae that are united posteriorly. The spinous and transverse processes protrude from the neural arch. The superior and inferior articular facets lie at the root of the transverse process. The term "functional spinal unit" ("FSU") refers to the entire motion segment: the anterior disc and the posterior facet joints, along with the supporting ligaments and connective tissues.

The spine as a whole is a highly flexible structure capable of a high degree of curvature and twist in nearly every direction. However, genetic or developmental irregularities, trauma, chronic stress, and degenerative wear can result in spinal pathologies for which surgical intervention may be necessary.

It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the anulus to buckle in areas where the laminated plies are loosely bonded. As the overlapping laminated plies of the anulus begin to buckle and separate, either circumferential or radial anular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. U.S. Pat. No. 4,863,477 discloses a resilient spinal disc prosthesis intended to replace the resiliency of a natural human spinal disc. U.S. Pat. No. 5,192,326 teaches a prosthetic nucleus for replacing just the nucleus portion of a human spinal disc.

In other cases it is desired to fuse the adjacent vertebrae together after removal of the disc, sometimes referred to as "intervertebral fusion" or "interbody fusion."

Many techniques and instruments have been devised to perform intervertebral fusion. There is common agreement that the strongest intervertebral fusion is the interbody (between the lumbar bodies) fusion, which may be augmented by a posterior or facet fusion. In cases of intervertebral fusion, either structural bone or an interbody fusion cage filled with morselized bone is placed centrally within the space where the spinal disc once resided. Multiple cages or bony grafts may be used within that space.

Such practices are characterized by certain disadvantages, most important of which is the actual morbidity of the procedure itself. Placement of rigid cages or structural grafts in the interbody space either requires an anterior surgical approach, which carries certain unavoidable risks to the viscous structures overlying the spine (intestines, major blood vessels, and the ureter), or they may be accomplished from a posterior surgical approach, thereby requiring significant traction on the overlying nerve roots. The interval between the exiting and traversing nerve roots is limited to a few millimeters and does not allow for safe passage of large intervertebral devices, as may be accomplished from the anterior approach. Alternatively, the anterior approach does not allow for inspection of the nerve roots, is not suitable alone for cases in which the posterior elements are not competent, and most importantly, the anterior approach is associated with very high morbidity and risk where there has been previous anterior surgery.

Another significant drawback to fusion surgery in general is that adjacent vertebral segments show accelerated deterioration after a successful fusion has been performed at any level. The spine is by definition stiffer after the fusion procedure, and the natural body mechanics place increased stress on levels proximal to the fused segment. Other drawbacks include the possibility of "flat back syndrome" in which there is a disruption in the natural curvature of the spine. The vertebrae in the lower lumbar region of the spine reside in an arch referred as having a sagittal alignment. The sagittal alignment is compromised when adjacent vertebral bodies that were once angled toward each other on their posterior side become fused in a different, less angled orientation relative to one another. Finally, there is always the risk that the fusion attempt may fail, leading to pseudoarthrosis, an often painful condition that may lead to device failure and further surgery.

Conventional interbody fusion cages generally comprise a tubular metal body having an external surface threading. They are inserted transverse to the axis of the spine, into preformed cylindrical holes at the junction of adjacent vertebral bodies. Two cages are generally inserted side by side with the external threading tapping into the lower surface of the vertebral bone above, and the upper surface of the vertebral bone below. The cages include holes through which the adjacent bones are to grow. Additional materials, for example autogenous bone graft materials, may be inserted into the hollow interior of the cage to incite or accelerate the growth of the bone into the cage. End caps are often utilized to hold the bone graft material within the cage.

These cages of the prior art have enjoyed medical success in promoting fusion and grossly approximating proper disc height. As previously discussed, however, cages that would be placed from the safer posterior route would be limited in size by the interval between the nerve roots. It would therefore, be a considerable advance in the art to provide a fusion implant assembly which could be expanded from within the intervertebral space, thereby minimizing potential trauma to the nerve roots and yet still providing the ability to restore disc space height.

Ultimately though, it is important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. Thus, it would be an even greater advance in the art to provide an implant assembly that does not promote fusion, but instead closely mimics the biomechanical action of the natural disc cartilage, thereby permitting continued normal motion and stress distribution.

SUMMARY OF THE INVENTION

Accordingly, an artificial functional spinal unit (FSU) is provided comprising, generally, an expandable artificial intervertebral implant that can be placed via a posterior surgical approach and used in conjunction with one or more artificial facet joints to provide an anatomically correct range of motion. Expandable artificial intervertebral implants in both lordotic and non-lordotic designs are disclosed, as well as lordotic and non-lordotic expandable cages for both PLIF (posterior lumber interbody fusion) and TLIF (transforaminal lumbar interbody fusion) procedures. The expandable implants may have various shapes, such as round, square, rectangular, banana-shaped, kidney-shaped, or other similar shapes. By virtue of their posteriorly implanted approach, the disclosed artificial FSU's allow for posterior decompression of the neural elements, reconstruction of all or part of the natural functional spinal unit, restoration and maintenance of lordosis, maintenance of motion, and restoration and maintenance of disc space height.

The posterior implantation of an interbody device provides critical benefits over other anterior implanted devices. Placement of posterior devices that maintain mobility in the spine have been limited due to the relatively small opening that can be afforded posteriorly between the exiting and transversing nerve roots. Additionally, placement of posterior interbody devices requires the removal of one or both facet joints, further destabilizing the spine. Thus conventional posteriorly placed interbody devices have been generally limited to interbody fusion devices.

Since a properly functioning natural FSU relies on intact posterior elements (facet joints) and since it is necessary to remove these elements to place a posterior interbody device, a two-step procedure is disclosed that allows for placement of an expandable intervertebral implant and replacement of one or both facets that are necessarily removed during the surgical procedure. The expansile nature of the disclosed devices allow for restoration of disc height once inside the vertebral interspace. The expandable devices are collapsed prior to placement and then expanded once properly inserted in the intervertebral space. During the process of expansion, the endplates of the natural intervertebral disc, which essentially remain intact after removal or partial removal of the remaining natural disc elements, are compressed against the device, which thereby facilitates bony end growth onto the surface of the artificial implant. Once the interbody device is in place and expanded, the posterior element is reconstructed with the disclosed pedicle screw and rod system, which can also be used to distract the disk space while inserting the artificial implant. Once the interbody device is in place and expanded, the posterior element is further compressed, again promoting bony end growth into the artificial implant. This posterior compression allows for anterior flexion but replaces the limiting element of the facet and interspinous ligament and thereby limits flexion to some degree, and in doing so maintains stability for the anteriorly located interbody device.

The posterior approach avoids the potential risks and morbidity of the anterior approach, which requires mobilization of the vascular structures, the ureter, and exposes the bowels to risk. Also, the anterior approach does not offer the surgeon an opportunity to view the posterior neural elements and thereby does not afford an opportunity for decompression of those elements. Once an anterior exposure had been utilized a revision procedure is quite risky and carries significant morbidity.

The artificial FSU generally comprises an expandable intervertebral implant and one or more artificial facet joints. The expandable intervertebral implant generally comprises a pair of spaced apart plate members, each with a vertebral body contact surface. The general shape of the plate members may be round, square, rectangular, banana shaped, kidney shaped, or some other similar shape, depending on the desired vertebral implantation site. Because the artificial intervertebral implant is to be positioned between the facing surfaces of adjacent vertebral bodies, the plate members are arranged in a substantially parallel planar alignment (or slightly offset relative to one another in accordance with proper lordotic angulation) with the vertebral body contact surfaces facing away from one another. The plate members are to mate with the vertebral bodies so as to not rotate relative thereto, but rather to permit the spinal segments to axially compress and bend relative to one another in manners that mimic the natural motion of the spinal segment. This natural motion is permitted by the performance of an expandable joint insert, which is disposed between the plate members. The securing of the plate members to the vertebral bone is achieved through the use of a osteoconductive scaffolding machined into the exterior surface of each plate member. Alternatively, a mesh of osteoconductive surface may be secured to the exterior surface of the plate members by methods known in the art. The osteoconductive scaffolding provides a surface through which bone may ultimately grow. If an osteoconductive mesh is employed, it may be constructed of any biocompatible material, both metal and non-metal. Each plate member may also comprise a porous coating (which may be a sprayed deposition layer, or an adhesive applied beaded metal layer, or other suitable porous coatings known in the art, i.e. hydroxy appetite). The porous coating permits the long-term ingrowth of vertebral bone into the plate member, thus permanently securing the prosthesis within the intervertebral space.

In more detail, the expandable artificial implant of the present invention comprises four parts: an upper body, a lower body, an expandable joint insert, that fits into the lower body, and an expansion device, which may be an expansion plate, screw, or other similar device. The upper body generally comprises a substantially concave inferior surface and a substantially planar superior surface. The substantially planar superior surface of the upper body may have some degree of convexity to promote the joining of the upper body to the intact endplates of the natural intervertebral disc upon compression. The lower body generally comprises a recessed channel, having a rectangular cross-section, which extends along the superior surface of the lower body in the medial-lateral direction and substantially conforms to the shape of the upper and lower bodies. The lower body further comprises a substantially planar inferior surface that may have some degree of convexity to promote the joining of the lower body to the intact endplates of the natural intervertebral disc upon compression. The expandable joint insert resides within the channel on the superior surface of the lower body. The expandable joint insert has a generally flat inferior surface and a substantially convex superior surface that articulates with the substantially concave inferior surface of the upper body. Prior to expansion of the artificial implant, the generally flat inferior surface of the expandable joint insert rests on the bottom surface of the channel. The expandable joint insert is raised above the bottom of the channel by means of an expansion screw, an expansion plate, or other similar device, that is inserted through an expansion hole or slot. The expansion hole or slot is disposed through the wall of the lower body formed by the channel. The expansion hole or slot gives access to the lower surface of the channel and is positioned such that the expansion device can be inserted into the expansion hole or slot via a posterior surgical approach. As the expansion device is inserted through the expansion slot, into the channel, and under the expandable joint insert, the expandable joint insert is raised above the floor of the channel and lifts the upper body above the lower body to the desired disc height. The distance from the inferior surface of the lower body and the superior surface of the upper body should be equal to the ideal distraction height of the disk space. As the artificial implant is flexed and extended, the convex superior surface of the expandable joint insert articulates with the concave inferior surface of the upper body.

After the insertion and expansion of the expandable intervertebral implant, the posterior facet joints may be reconstructed by employing the disclosed artificial facet joints. One embodiment of the artificial facet joint generally comprises a lower and upper multi-axial pedicle screw joined by a rod bridging the vertebral bodies above and below the artificial implant. The rod comprises a washer-type head at its lower (caudad) end. The rod fits into the heads of the pedicle screws and a top loaded set screw is placed in the pedicle screw heads. The disclosed pedicle screw system may employ different types of pedicle screws so that the top loaded set screw may or may not lock down on the rod depending on surgeon preference. If a non-locking pedicle screw is used the caudad end remains fully multi-axial. The upper (cephalad) end of the rod is held within the head of the upper pedicle screw with a set screw which locks down on the rod and eliminates any rod movement at the cephalad end, which by nature has limited multi-axial function. In an alternative embodiment of an artificial facet joint, the rod may comprise washer-type heads on both ends (caudad and cephalad) so that both pedicle screws can be of the non-locking variety. In the event of a two level surgical procedure, three pedicle screws would be employed with a single rod, which would have washer-type heads at both ends. The middle pedicle screw would be a locking-type and the upper most and lower most pedicle screws would be of the non-locking variety.

In addition, another embodiment of the artificial facet joint is disclosed that generally comprises two locked pedicle screws joined by a rod having a ball and socket joint centrally located on the rod between the two pedicle screws. The locking of the pedicle screws prevents the screw head from swiveling, but allows rotation and translation of the rod.

In instances where a fusion procedure is unavoidable, a PLIF and TLIF cage are disclosed that utilize the expansion principal of the functional artificial intervertebral implant. The cage generally comprises three parts: An external body, an internal body, and an expansion device. The external and internal bodies will have substantially the same shape and will be shaped accordingly to the procedures for which they will be used, more specifically, a rectangular cage is employed for a PLIF procedure and round or banana shaped cage is employed for the TLIF procedure. Both the external and internal bodies comprise a mesh structure in which an osteoconductive substance can be placed (i.e. morsilized autograph or an osteobiologic substitute). The external body of the cage contains an internal void space that houses the internal body. The external body further comprises an expansion window on its superior surface through which the internal body is raised upon expansion of the cage. The internal body comprises a planar plate member that is slightly larger than the expansion window in the superior surface of the external body such that when the cage is expanded the planar plate member secures itself against the interior side of the expansion window, thereby interlocking the external and internal bodies and eliminating mobility between the two bodies. Similar to the functional expandable implant, an expansion device is placed through an expansion slot. The expansion device lifts the internal body relative to the external body, interlocking the planar plate member of the internal body against the interior of the expansion window, and pushing the mesh structure of the internal body through the expansion window and above the superior surface of the external body. Varying the height of the expansion device and the dimensions of the external and internal bodies allows for various distraction heights to regain disc space. As with the functional intervertebral implant, the PLIF and TLIF cages may take the form of either an expandable lordotic cage or a non-lordotic cage.

BRIEF DESCRIPTION OF THE DRAWINGS

FIG. 3b is a side cross-sectional view of the banana-shaped, expandable intervertebral implant shown in FIG. 3a.

FIG. 12a is a top view of an expandable PLIF cage in accordance with the present invention.

FIG. 12b is a side cross-sectional view of an expandable PLIF cage in accordance with the present invention prior to expansion.

FIG. 12c is a side cross-sectional view of an expandable PLIF cage in accordance with the present invention following expansion.

FIG. 17a is a top view of a banana-shaped expandable intervertebral implant featuring a round expandable joint insert.

PREFERRED EMBODIMENTS OF THE INVENTION

In the following detailed description of the preferred embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention.

Figure 1:
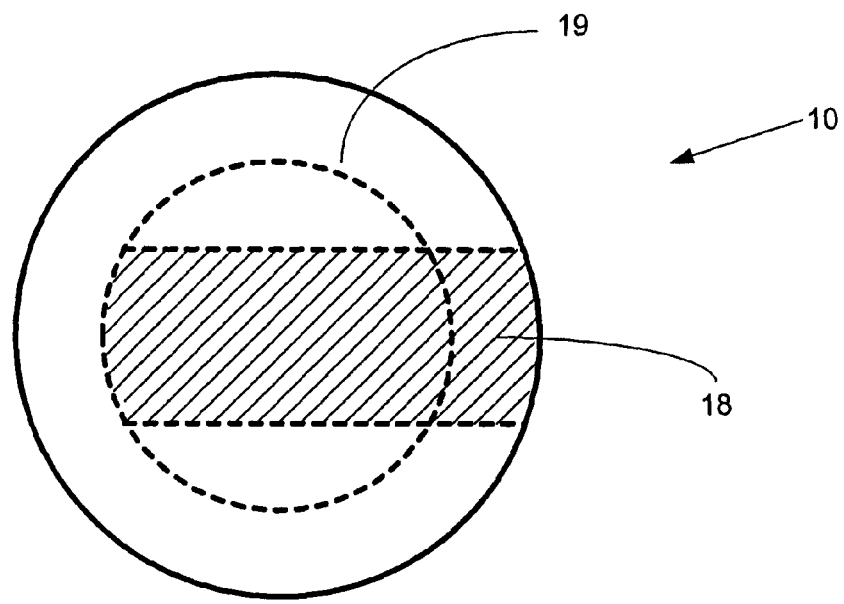
FIG. 1 is a top view of a round, expandable intervertebral implant of the present invention.
Figure 2:
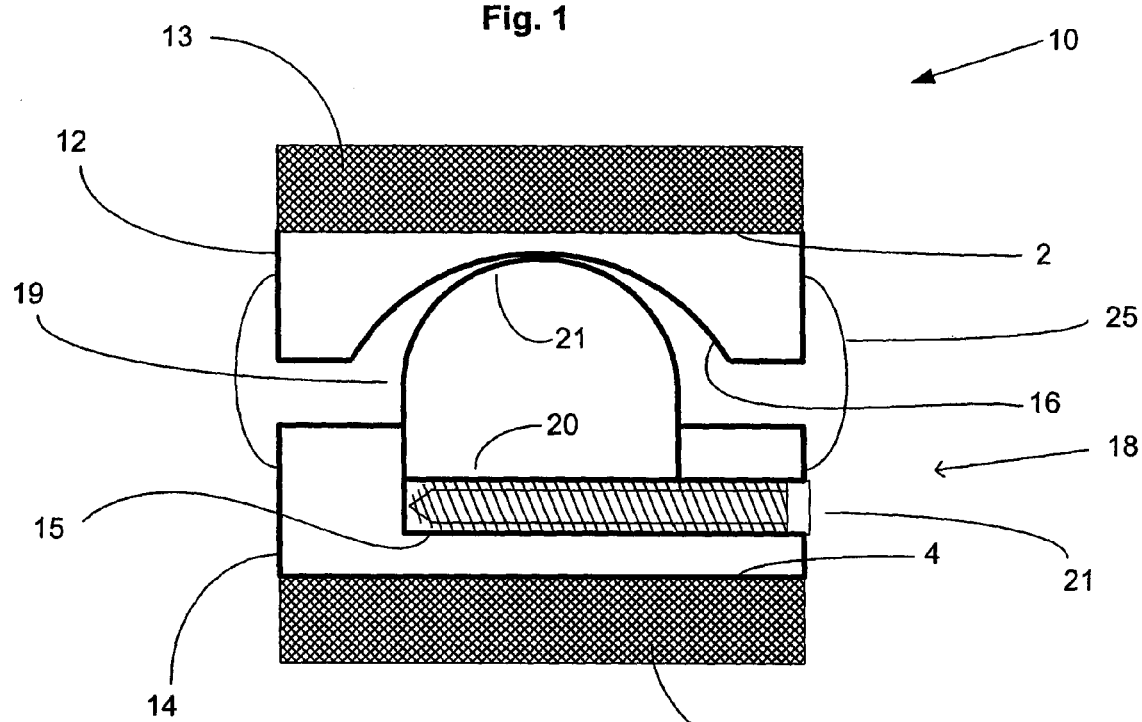
FIG. 2 is a side cross-sectional view of the round, expandable intervertebral implant shown in FIG. 1.

FIGS. 1 and 2 show a round, expandable artificial intervertebral implant designated generally at 10. The device is implemented through a posterior surgical approach by making an incision in the anulus connecting adjacent vertebral bodies after removing one or more facet joints. The natural spinal disc is removed from the incision after which the expandable artificial intervertebral implant is placed through the incision into position between the vertebral bodies. The implant is preferably made of a biocompatible metal having a non-porous quality and a smooth finish, however, it may also be constructed of ceramic or any other suitable inert material.

The expandable artificial intervertebral implant 10 generally comprises an upper body 12 and a lower body 14 in a substantially parallel planar configuration. The superior surface 2 of the upper body 12 and the inferior surface 4 of the lower body 14 comprise a machined osteoconductive scaffolding 13 through which the bone may ultimately grow. Osteoconductive scaffolding 13 may also include spines or barbs that project into and secure against the bony endplates of the adjacent bony vertebral bodies upon expansion of the joint and minimize the possibility of sublaxation and/or dislocation. The upper body 12 has a substantially concave inferior surface 16. The lower body 14 has a channel 15 on its superior surface 17. Channel 15 has a rectangular cross-section that extends along the lower body 14 in the medial-lateral direction and substantially conforms to the shape of the upper 12 and lower 14 bodies. An expandable joint insert 19 resides within the channel 15 on the lower body. The expandable joint insert 19 has a generally flat inferior surface 20 and a substantially convex superior surface 21 that articulates with the substantially concave inferior surface 16 of the upper body 12. The expandable joint insert 19 is lifted from the bottom of channel 15 by means of an expansion screw 21, or other device, that is inserted between the generally flat inferior surface 20 of the expandable joint insert 19 and the bottom of the channel 15 extending along the lower body 14 through an expansion slot 18. A void space is created between the expandable joint insert 19 and the floor of the channel 15 in cross-sections not including the expansion device. A securing means, such as the cables 25, may be employed to ensure the upper body 12 and the lower body 14 remain intact during flexion and extension of the FSU. Alternative means for securing the upper body 12 and lower body 14 may also be employed, such as retaining pegs, torsion springs, or similar devices.

Figure 3A:
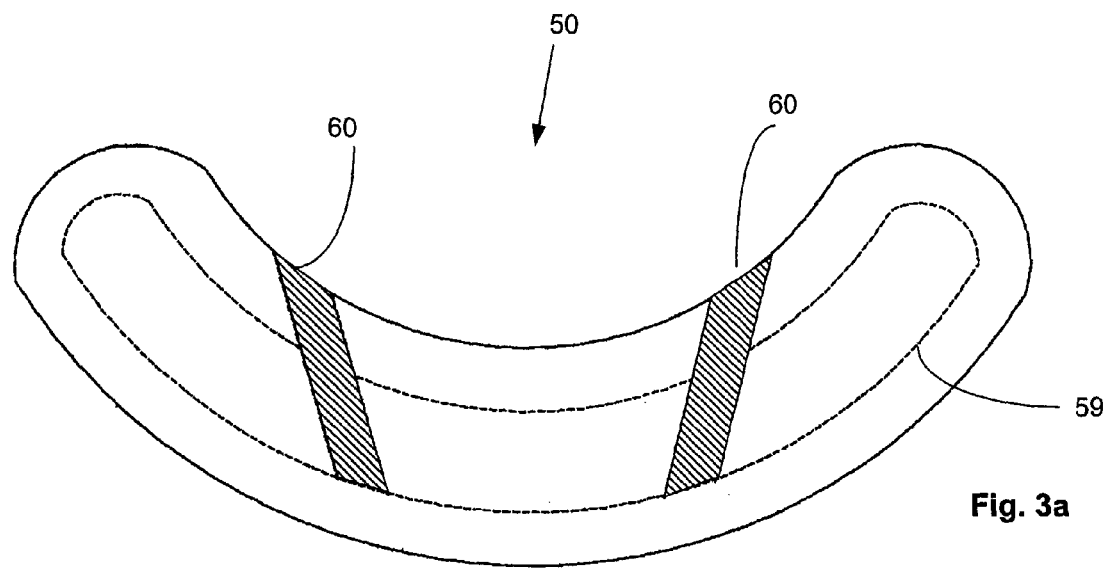
FIG. 3a is a top view of a banana-shaped, expandable intervertebral implant of the present invention.
Figure 3B:
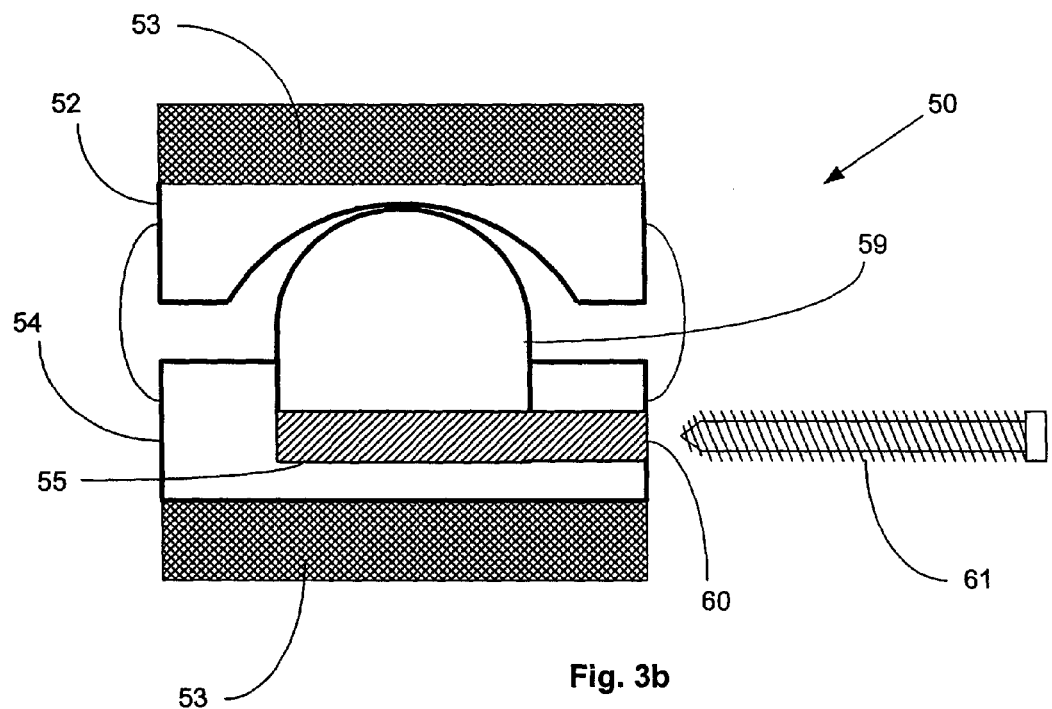

FIGS. 3a and 3b show a banana-shaped expandable artificial intervertebral implant 50. As with the round implant 10 shown in FIG. 1, the banana-shaped implant also comprises an upper body 52 and a lower body 54 in a substantially planar configuration, each having an external osteoconductive scaffolding 53. Note that the channel 55 and the expandable joint insert 59, which is disposed within the channel 55, may substantially conform to the shape of the upper 52 and lower 54 bodies. Alternatively, expandable joint insert 59 may have a different shape, such as oval or round, as compared the shape of the upper 52 and lower 54 bodies. Whereas the round expandable implant may comprise a single expansion device, the banana-shaped implant may contain one or more expansion devices 61 that are inserted into expansion slots 60. Otherwise, the cross-section of the banana-shaped implant is substantially similar to FIG. 2.

Figure 4A:
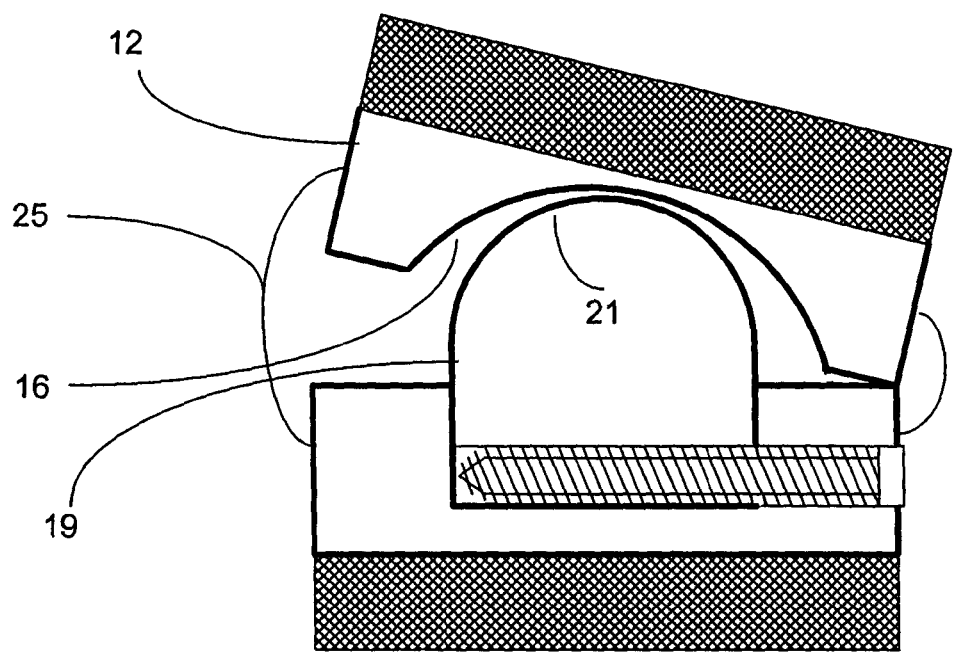
FIG. 4a is a cross-sectional illustration of an expandable intervertebral implant in compression.
Figure 4B:
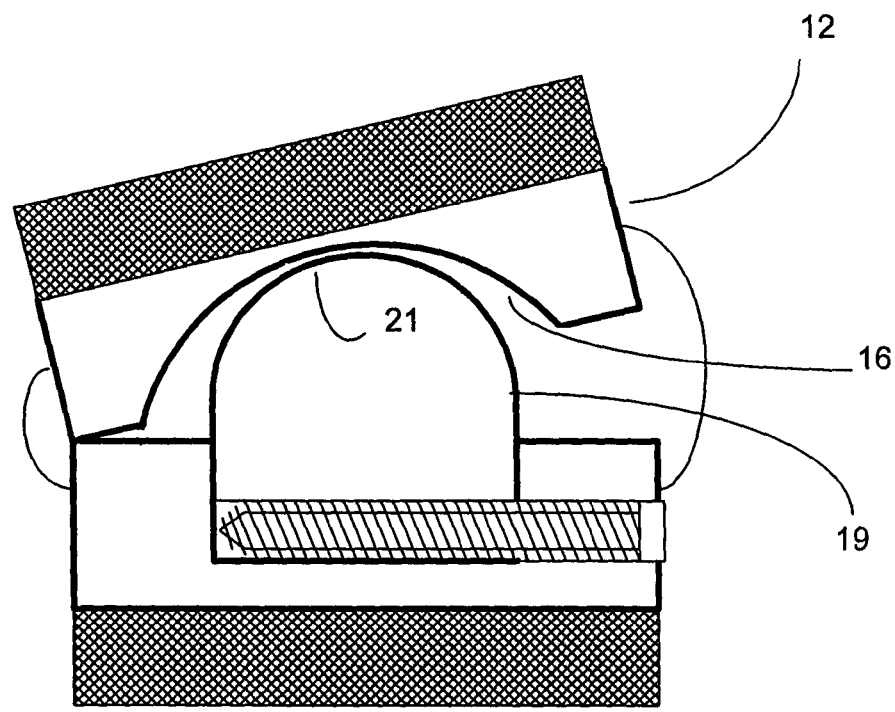
FIG. 4b is a cross-sectional illustration of an expandable intervertebral implant in flexion.

Turning to FIGS. 4a and 4b, an expandable artificial intervertebral implant is shown in flexion and extension, respectively. The concave inferior surface of 16 of upper body 12 articulates with the convex superior surface 21 of expandable joint insert 19. As stated above, securing means 25 may be employed to prevent dislocation of the implant.

Figure 5A:
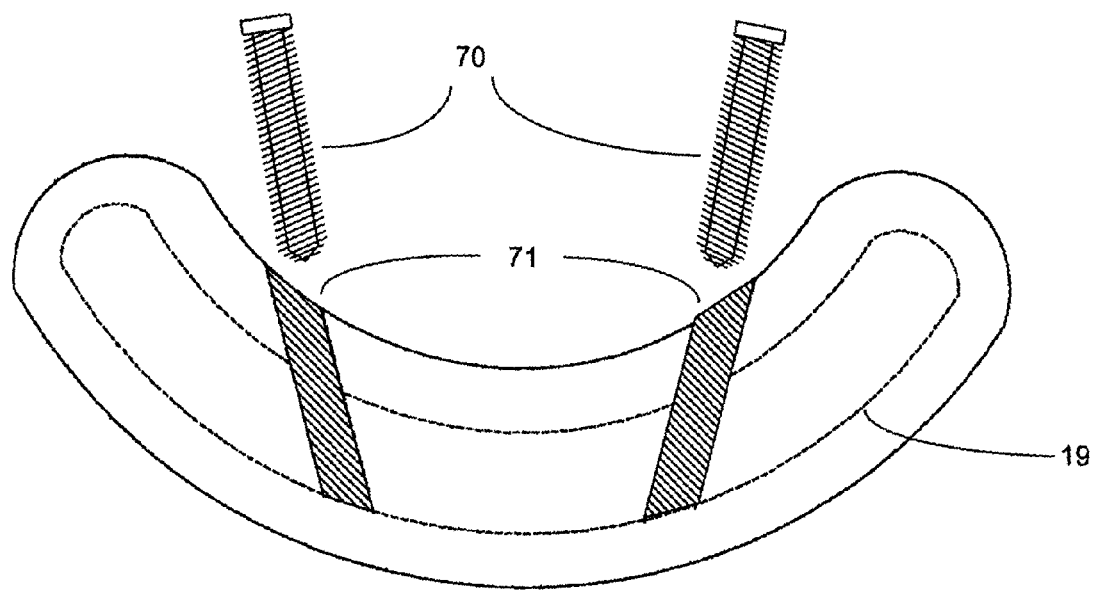
FIG. 5a is a top view of a banana-shaped, expandable intervertebral implant, illustrating the insertion of expansion screws to expand the joint.
Figure 5B:
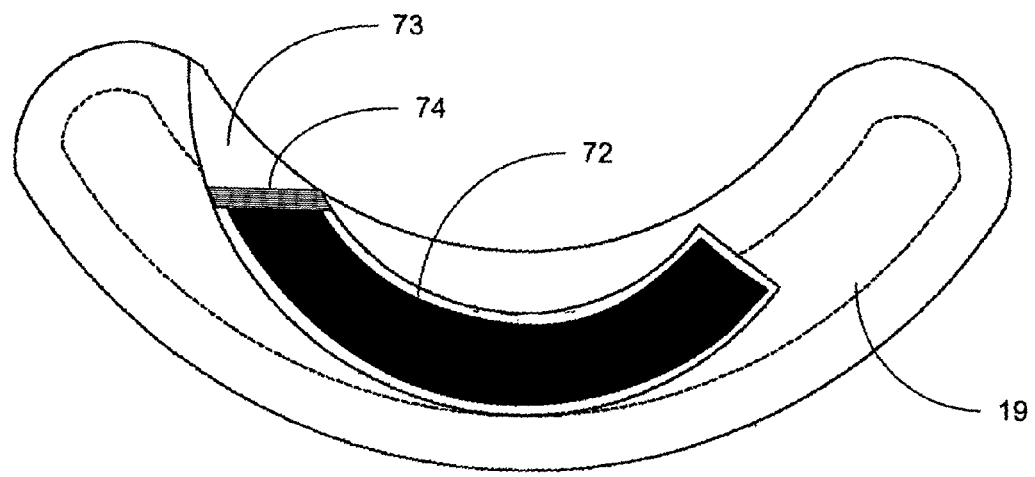
FIG. 5b is a top view of a banana-shaped, expandable intervertebral implant, illustrating the insertion of a non-threaded expansion device to expand the joint.

FIGS. 5a and 5b illustrate the insertion of expansion devices into a banana-shaped implant. The artificial intervertebral implant 50 in FIG. 5a employs expansion screws 70 to expand joint insert 19. One or more expansion screws 70 may be inserted through one or more threaded expansion slots 71. Alternatively, as shown in FIG. 5b, artificial implant 55 may employ a non-threaded expansion device 72 inserted through a non-threaded expansion slot 73 to accomplish the expansion of joint insert 19. The non-threaded expansion slot 73 preferably has an arcuate shape to facilitate insertion after the artificial disc prosthesis has been properly placed within the intervertebral space. The non-threaded expansion device 72 has substantially the same shape as expansion slot 73. A threaded end cap 74 maybe employed to retain the expansion device 72 inside the expansion slot 73.

Figure 6A:
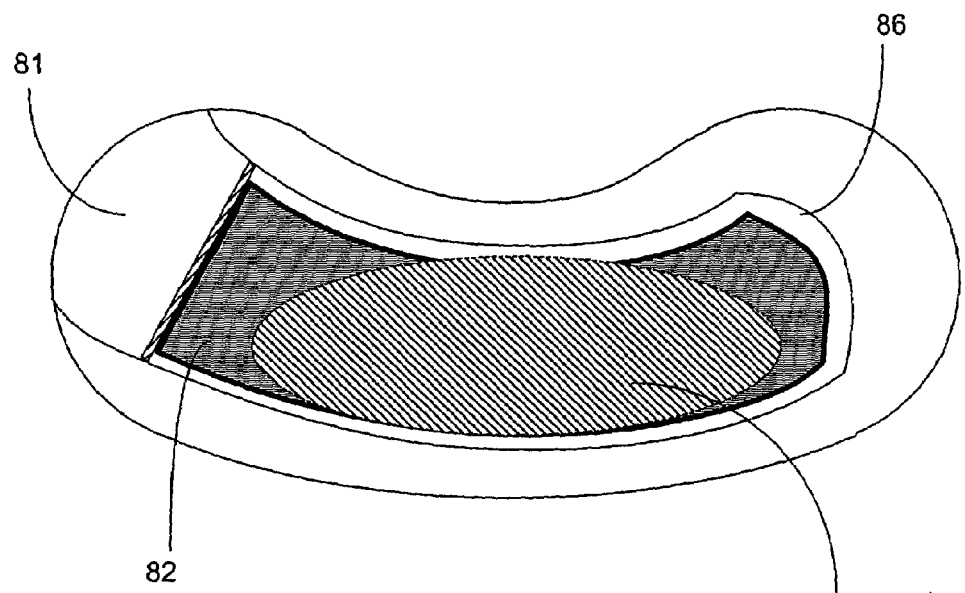
FIG. 6a is a top view of a banana-shaped, expandable intervertebral implant, illustrating the insertion of an expansion plate to expand the joint.
Figure 6B:
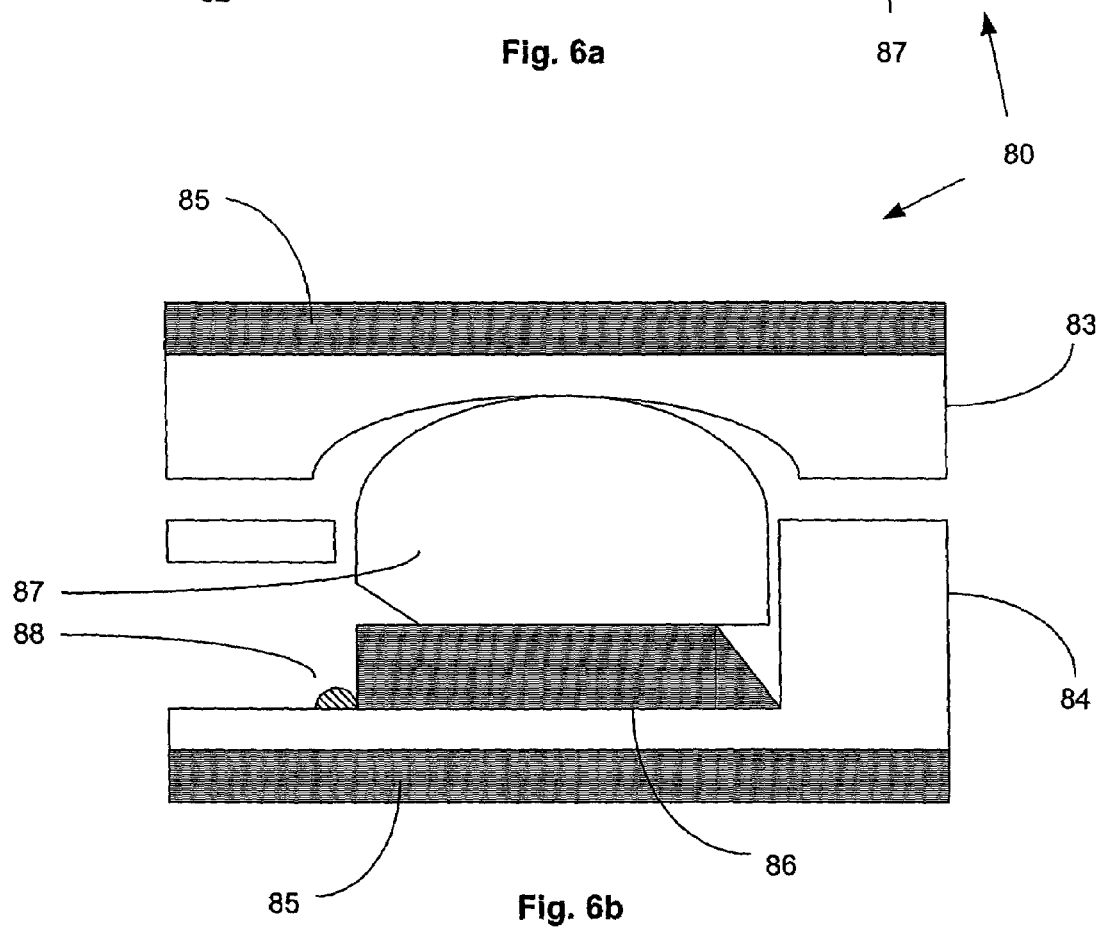
FIG. 6b is a side cross-sectional view of a banana-shaped, expandable intervertebral implant, illustrating the insertion of an expansion plate to expand the joint.

FIGS. 6a and 6b illustrate an alternative embodiment of a non-threaded expansion device. As shown in FIG. 6a, a banana-shaped artificial intervertebral implant 80 having a wide expansion slot 81 on either the medial or lateral side of the implant 80. Expansion plate 82 may be impacted into place through expansion slot 81 after artificial implant 80 has been properly placed within the intervertebral space. Similar to the previously described embodiments, the artificial implant comprises an upper body 83 and a lower body 84 in a substantially planar configuration, each having an osteoconductive scaffolding 85 machined on their superior and inferior surfaces, respectively. Note that the channel 86, as well as expansion plate 82, substantially conforms to the shape of the upper 83 and lower 84 bodies. Joint insert 87 may generally conform to the shape of the upper 83 and lower 84 bodies, however, the its preferred shape for the banana-shaped implant 80 is more oval, or even more preferably round, to provide improved biomechanical motion of the implant. The bottom floor of channel 86 may also employ a locking lip 88 to ensure that the expansion plate 82 is properly installed and to minimize the potential for dislocating expansion plate 82.

Figure 6C:
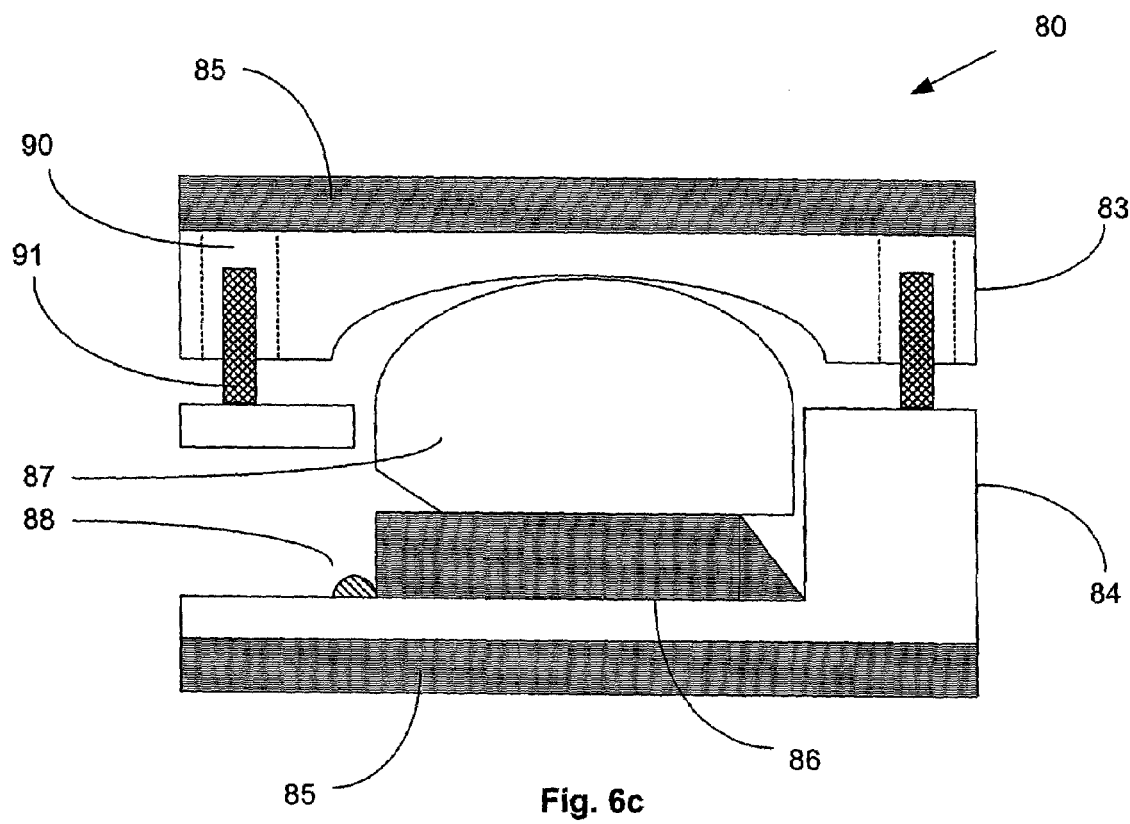
FIG. 6c is a side cross-sectional view of an expandable intervertebral implant, featuring retaining pegs.
Figure 6D:
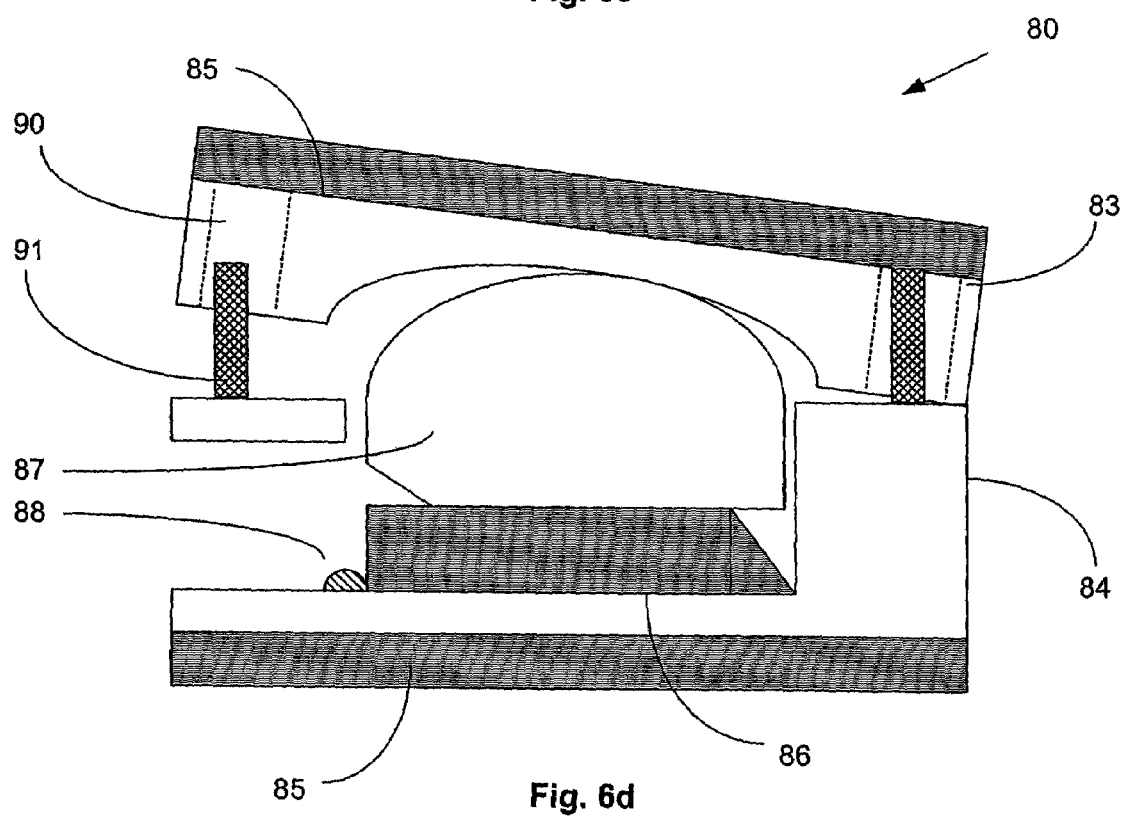
FIG. 6d is a side cross-sectional view of an expandable intervertebral implant in flexion, featuring retaining pegs.

FIGS. 6c and 6d illustrate another preferred embodiment of an expandable intervertebral implant featuring retaining pegs 91 to ensure against dislocation of upper body 83 from lower body 84 during flexion, extension and torsional motion. A plurality of retaining pegs 91 project substantially upward form the superior surface of lower body 84. On its' inferior surface, upper body 83 comprises a plurality of holes, or containment wells 90, dimensionally larger than captive pegs 91 and arranged such that when upper body 83 is properly positioned upon lower body 84, captive pegs 91 are housed within containment wells 90. As shown in FIG. 6d, when the intervertebral implant is flexed or extended, captive pegs 91 prohibit dislocation of upper body 83 from lower body 84. While the pegs and containment wells may be any shape, captive pegs 91 are preferably round and containment wells 90 are preferably oval in shape, which gives limited torsional mobility as well.

Figure 7A:
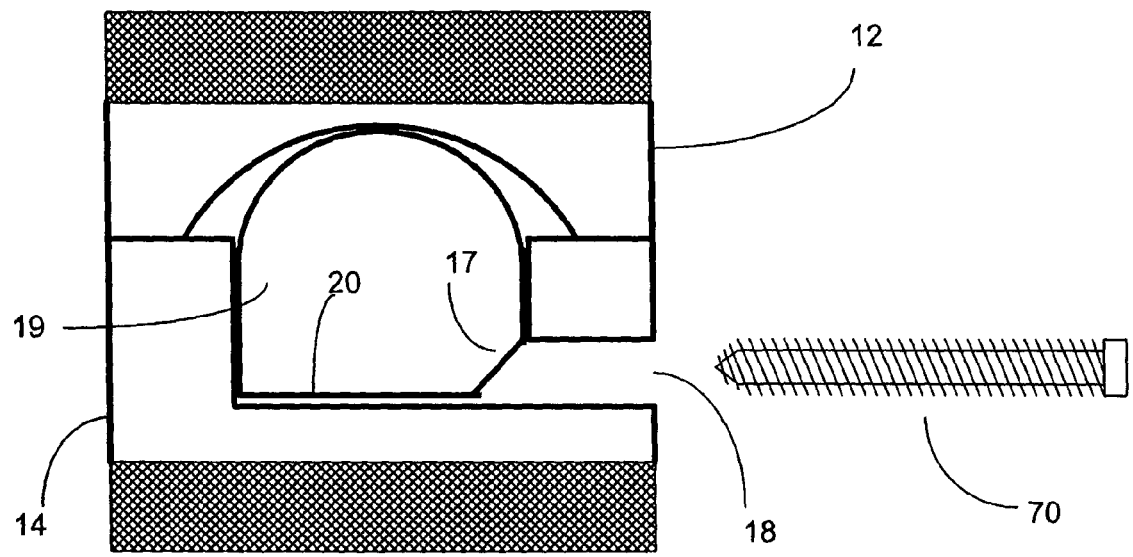
FIG. 7a is a cross-sectional view of an expandable intervertebral implant, prior to expansion.
Figure 7B:
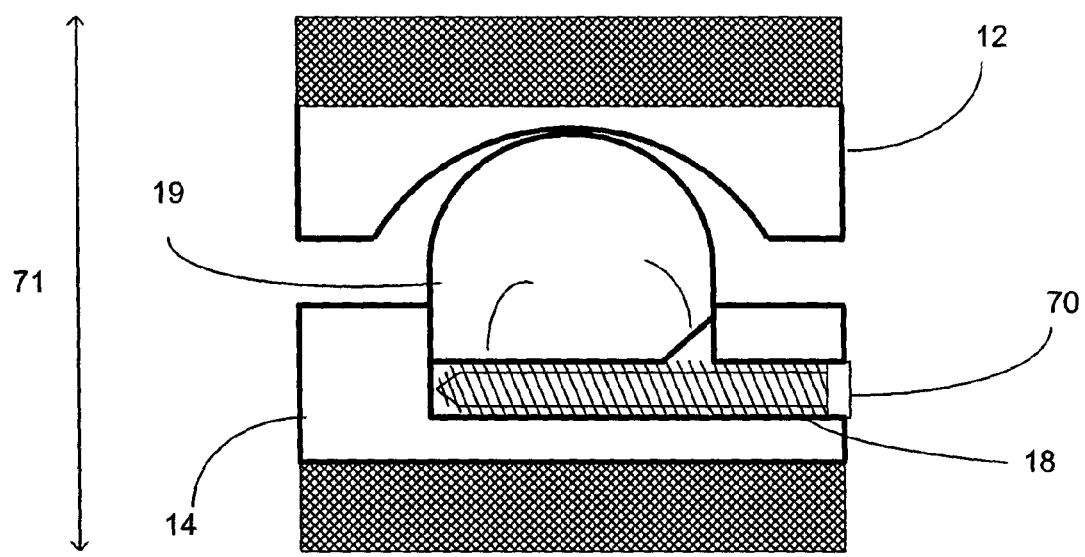
FIG. 7b is a cross-sectional view of an expandable intervertebral implant, following expansion.

FIGS. 7a and 7b illustrate the expansion of joint insert 19 in more detail. As shown in FIG. 7a and prior to expansion of joint insert 19, upper body 12 rests upon lower body 14 and the generally flat inferior surface 20 of joint insert 19 rests upon the bottom of channel 15, which extends along the lower body 14. Disposed along the generally flat inferior surface 20 of expandable joint insert 19 and adjacent to expansion slot 18, is a lifting notch 17 that engages with the expansion screw 70. Lifting notch 17 facilitates the lifting of expandable joint insert 19 and allows expansion screw 70 to come into contact with the generally flat inferior surface 20 of joint insert 19. Once inserted, as shown in FIG. 7b, the generally flat inferior surface 20 of expandable joint insert 19 rests upon expansion screw 70 and the upper body 12 is lifted above lower body 14 to the desired intervertebral disc height 71.

Figure 8:
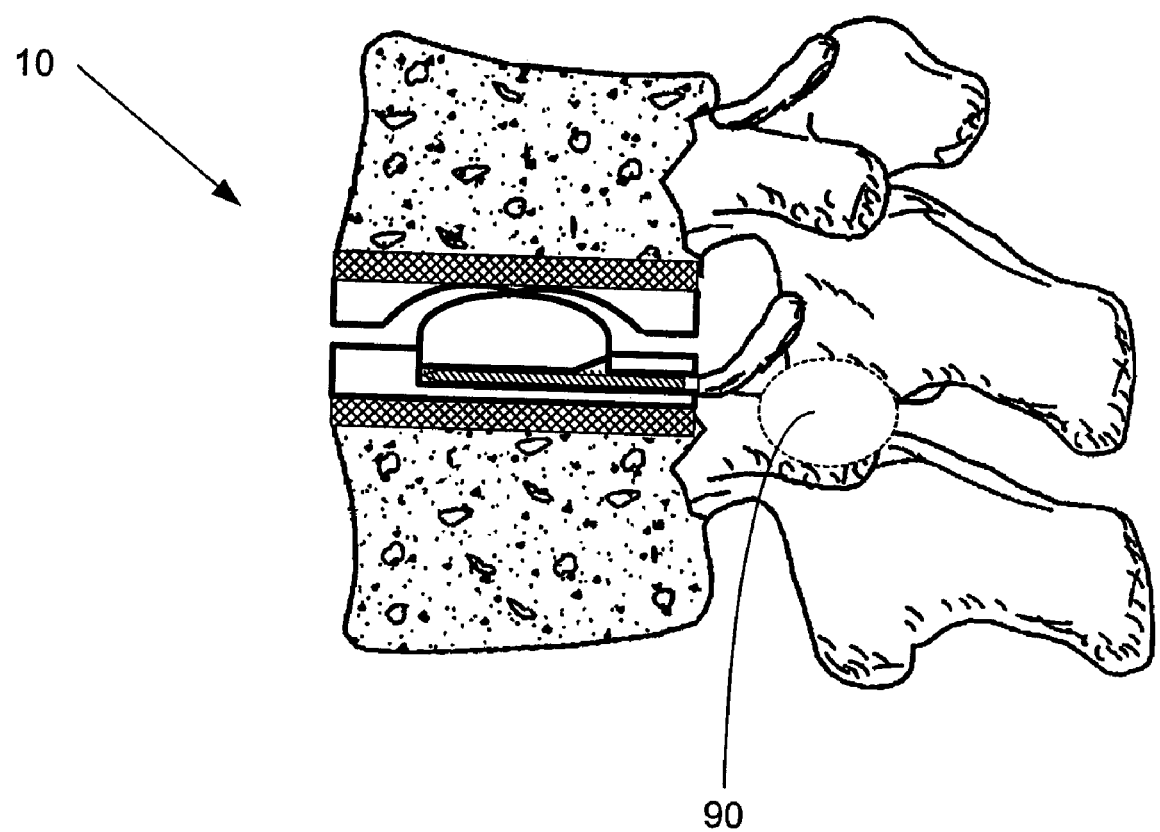
FIG. 8 is a side perspective view illustrating placement of an expandable intervertebral implant within an intervertebral space.

FIG. 8 shows an expandable artificial intervertebral implant 10 inserted into the spinal column. Note that the expandable artificial implant 10 is posteriorly inserted and expanded through void space 90, which is created by removal of a facet joint.

The disclosed techniques of expanding an artificial implant by inserting an expansion plate or similar device may also be employed to expand a PLIF or TLIF cage. As shown in FIGS. 12a, 12b and 12c, a PLIF cage 300 is disclosed comprising a substantially rectangular external cage element 301 housing an internal expandable element 302. The PLIF cage element 301 has an osteoconductive mesh structure 303, in which an osteoconductive substance can be placed, on its inferior surface 304 and an expansion window 305 located on its superior surface 306. The internal expandable element 302 comprises a generally planar plate member 307 having an inferior 308 and superior surface 309. A second osteoconductive mesh structure 310 is secured upon the superior surface 309 of the planar plate member 307 of the internal expandable element 302. The inferior surface 308 of the planar plate member 307 has a lifting notch 311 to facilitate the expansion of the device upon installation of the expansion plate 312. The expansion plate 312 is inserted into the posteriorly located expansion slot 313 of the PLIF external cage element 301 and engages the lifting notch 311 of the planar plate member 307 of the internal expandable element 302. Locking lip 314 located within expansion slot 313 minimizes the potential of expansion plate 312 dislocation.

Figure 12D:
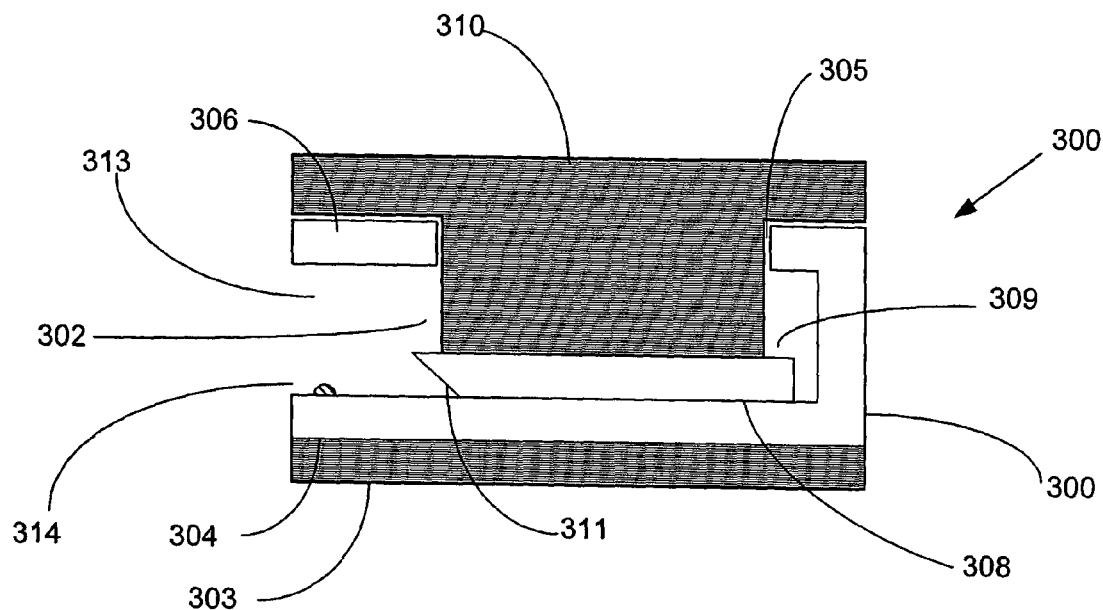
FIG. 12d is a side cross-sectional view of an expandable TLIF cage in accordance with the present invention prior to expansion.
Figure 12E:
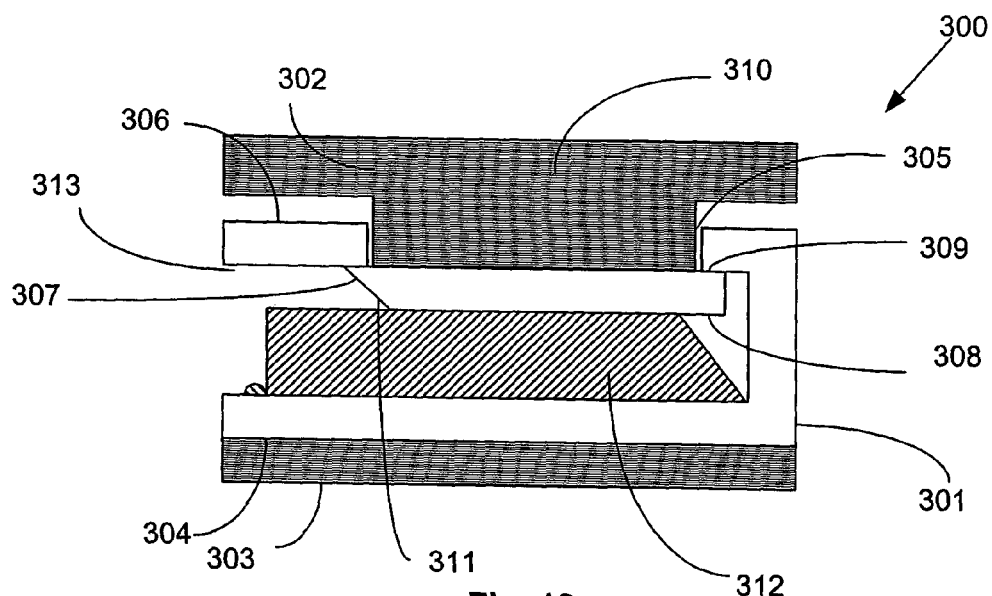
FIG. 12e is a side cross-sectional view of an expandable TLIF cage in accordance with the present invention following expansion.

FIGS. 12d and 12e show a TLIF cage similar to the PLIF cage described above. The primary difference between the TLIP cage and the PLIF cage is that the TLIF cage comprises a t-shaped cross-sectional osteoconductive mesh structure 310 secured upon the superior surface 309 of the planar plate member 307 of the internal expandable element 302 such that the osteoconductive mesh structure 310 overhangs the superior surface 306 of the external cage element 301. Thus providing more surface area between the osteoconductive mesh structure 310 and the bony endplates within the intervertebral space.

Figure 9A:
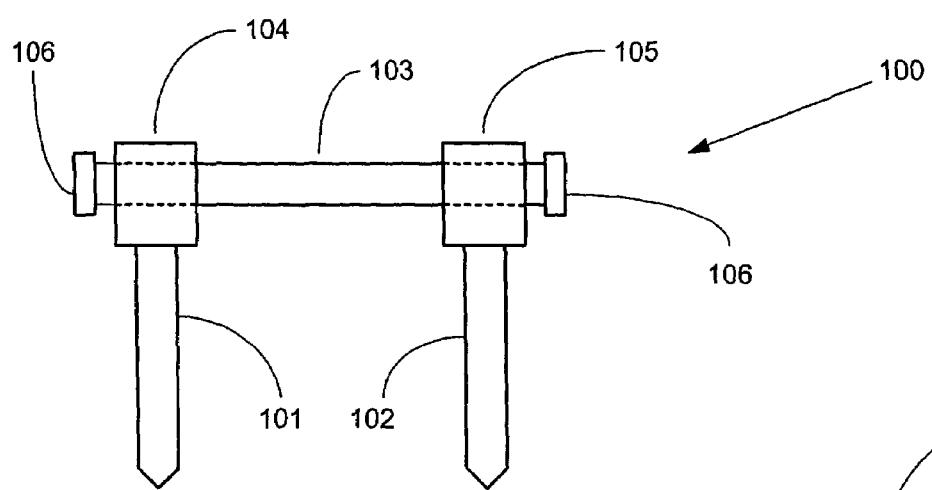
FIG. 9a is a side view of an artificial facet joint of the present invention, featuring a rod with two washer-type heads.

One preferred embodiment of an artificial facet joint 100 in accordance with the present invention is shown in FIG. 9a. Artificial facet joint 100 comprises an upper pedicle screw 101 and a lower pedicle screw 102. Rod 103 is retained within the head 104 of upper pedicle screw 101 and the head 105 of lower pedicle screw 102. Rod 103 has washer-type ends 106 that allows for posterior compression, but not extension.

Figure 9B:
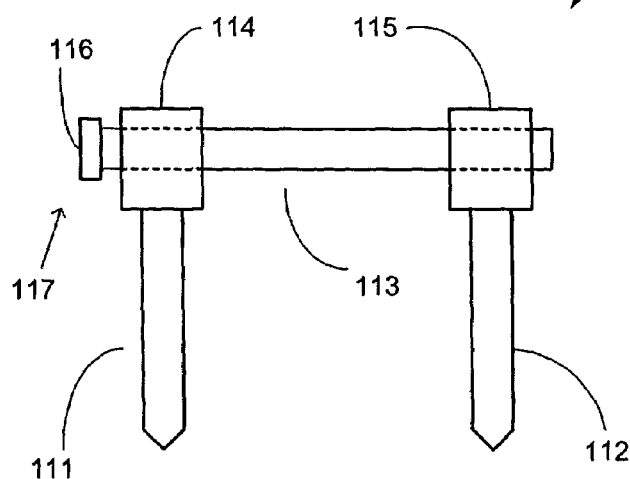
FIG. 9b is a side view of an artificial facet joint of the present invention, featuring a rod with a single washer-type head.
Figure 9C:
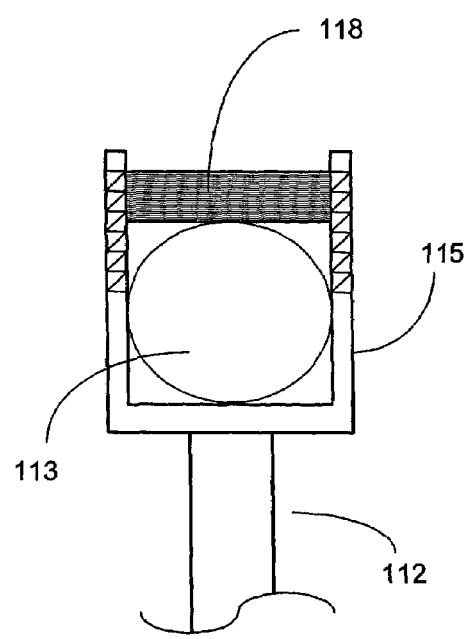
FIG. 9c is a cross-sectional view of a pedicle screw featuring a locking screw head.

Another preferred embodiment of an artificial facet joint 110 is shown in FIG. 9*b*. Rod 113 comprises a single washer-type end 116 on its lower end 117. The head 115 of upper pedicle screw 112 has a threaded locking screw 118, as shown in FIG. 9*c*, that holds rod 113 in place and prohibits the head 115 of pedicle screw 112 from swiveling, but allows rod 113 to rotate and translate through the head 115 of pedicle screw 102.

Figure 10:
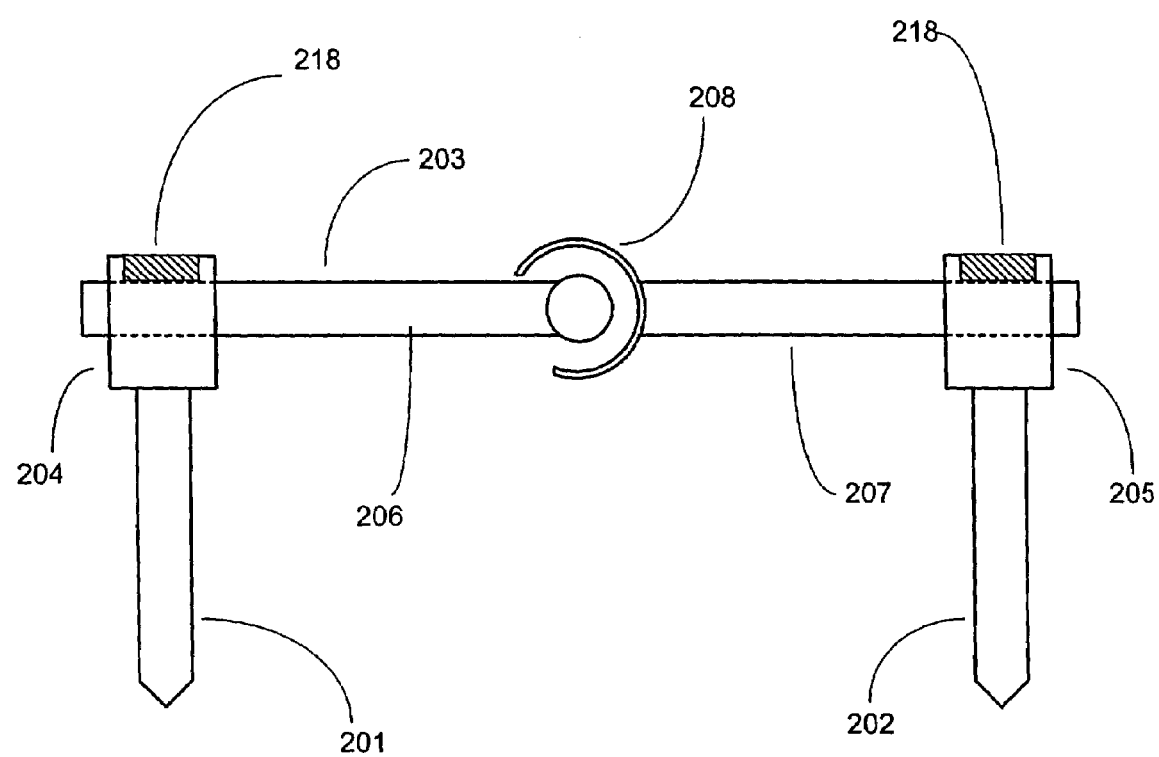
FIG. 10 is a side view of an artificial facet joint of the present invention, featuring a rod having a ball joint.

Another preferred embodiment of an artificial facet joint 200 is shown in FIG. 10. Artificial facet joint 200 generally comprises an upper pedicle screw 201 and a lower pedicle screw 202 and rod 203 retained within the heads of pedicle screws 201,202. Both pedicle screws 201,202 are secured with locking screws 218 that prevent the heads 204, 205 of pedicle screws 201,202 from swiveling, but allow rotation and translation of rod 203. Rod 203 comprises two rod members 206, 207 connected via a ball joint 208. Ball joint 208 allows for a generally upward rotation, away from the bony surfaces of the vertebrae to which they are secured, but prohibit a generally downward rotation, which would bring the ball joint in contact with the vertebrae to which they are secured.

Figure 11:
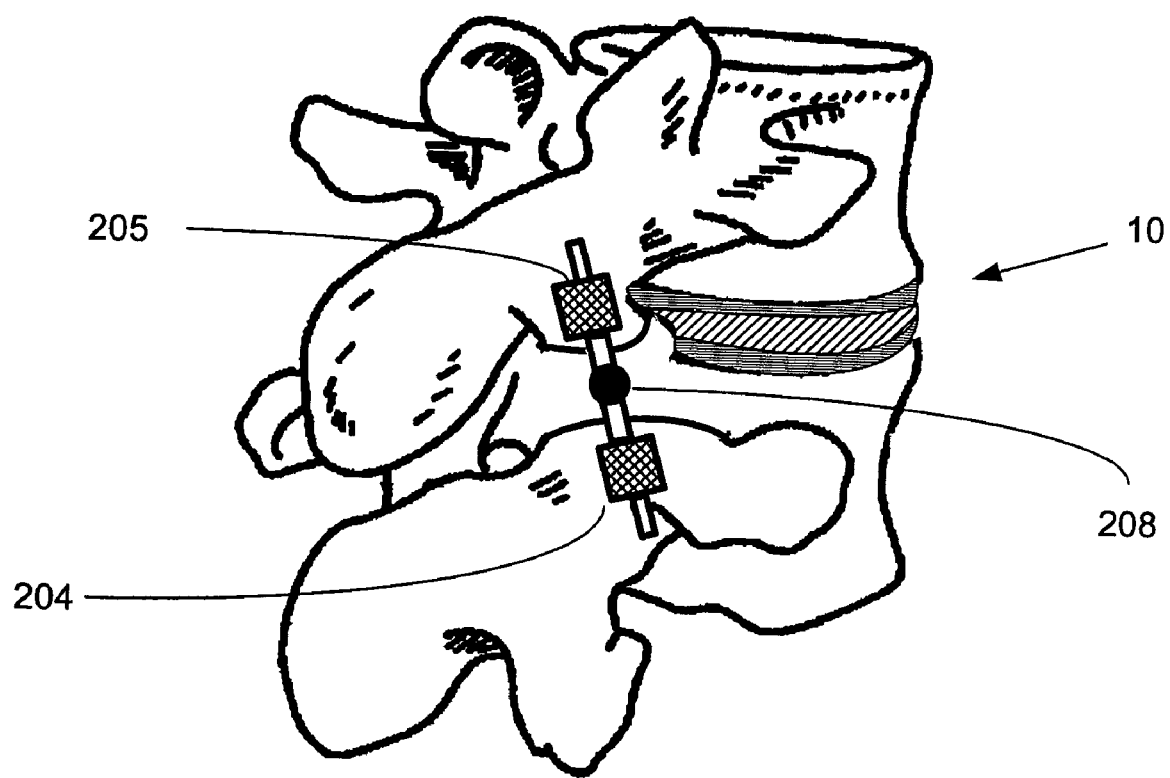
FIG. 11 is a posterior view of the spine after reconstruction and implantation of an artificial functional spinal unit including an expandable intervertebral implant and an artificial facet joint.

FIG. 11 shows the artificial facet joint 200 of FIG. 10 in place on the spinal column. Note that artificial intervertebral implant 10 has been posteriorly placed within the intervertebral space through the void created by the surgical removal of the natural facet joint. In addition, ball joint 208 generally rotates in the posterior (upward) direction during posterior compression to prevent impact upon the bony surfaces of the spine.

Figure 13A:
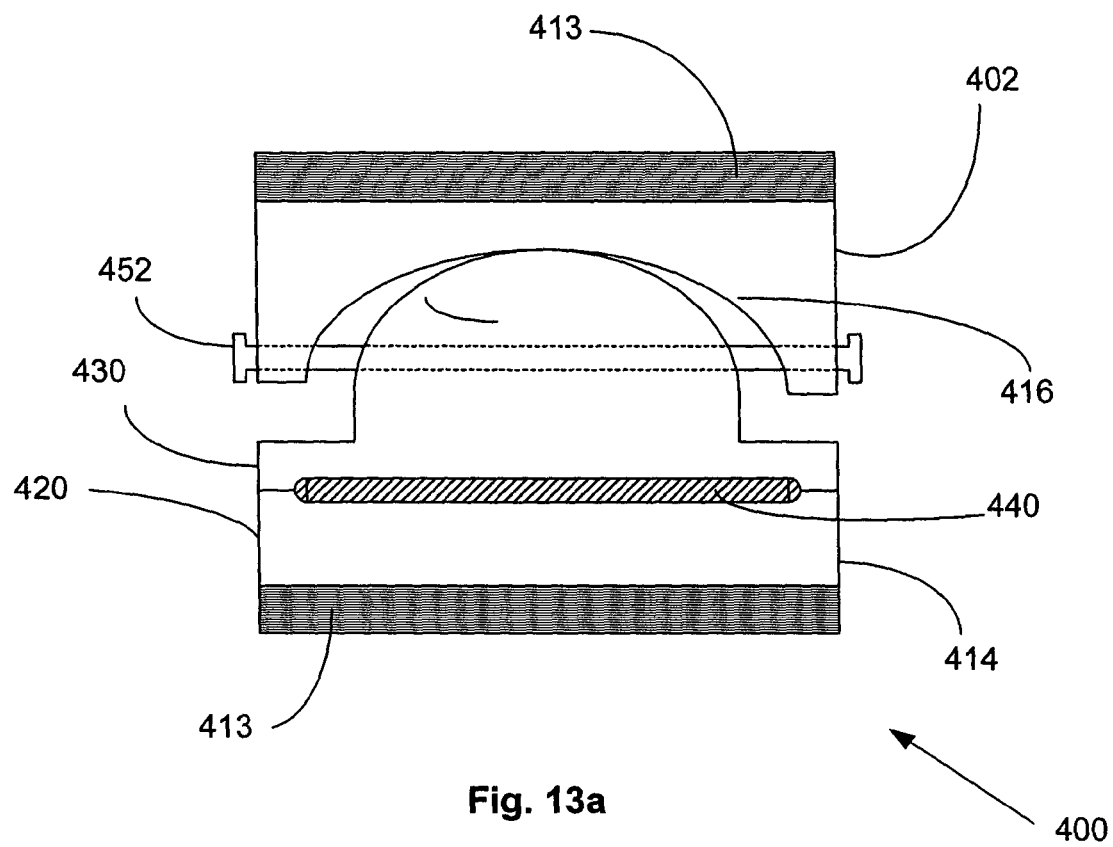
FIG. 13a is a posterior view of a banana-shaped lordotic expandable intervertebral implant.

FIGS. 13*a*, 13*b*, 14*a* and 14*b* illustrate a lordotic, banana-shaped expandable artificial intervertebral implant 400. The lumbar spine is lordotic, thus the anterior disc height is naturally larger than the posterior disc height. Therefore, an expandable artificial intervertebral implant for the lumbar spine must be capable of expanding into a lordotic position. FIG. 13*a* shows the lordotic expandable artificial intervertebral implant 400 from a posterior view. Lordotic expandable artificial intervertebral implant 400 generally comprises an upper body 412 and a lower hinged body 414 in a substantially planar configuration prior to expansion. The superior surface 402 of the upper body 412 and the inferior surface 404 of the lower hinged body 414 comprise an osteoconductive scaffolding 413 through which the bone may ultimately grow. The upper body 412 has a substantially concave inferior surface 416.

The lower hinged body 414 comprises a lower portion 420 and an upper portion 430. Lower portion 420 and upper portion 430 are posteriorly hinged via hinge 440. Hinge 440 effectively fixes the posterior disk height 460 (shown in FIG. 14*b*). Upper portion 430 of hinged body 414 has a generally flat inferior surface 431 and a substantially convex superior surface 432. The lower portion 420 has a substantially planar configuration prior to expansion. Located at the anterior end 421 of lower portion 420 is a rotational lifting mechanism 422. Once placed in the intervertebral space, the rotational lifting leg is rotationally engaged, thus lifting the anterior end 421 of the expandable artificial intervertebral implant 400 to achieve the desired anterior disc height 470 and proper lordosis. Securing notch 425 is located on the anterior end 421 of the upper portion 430 of hinged body 414. Securing notch 425 engages with rotational lifting mechanism 422 once the expandable artificial intervertebral implant 400 has been expanded. The height of rotational lifting mechanism 422 is determined by the desired proper lordosis when the intervertebral implant 400 is under neutral load.

Figure 14A:
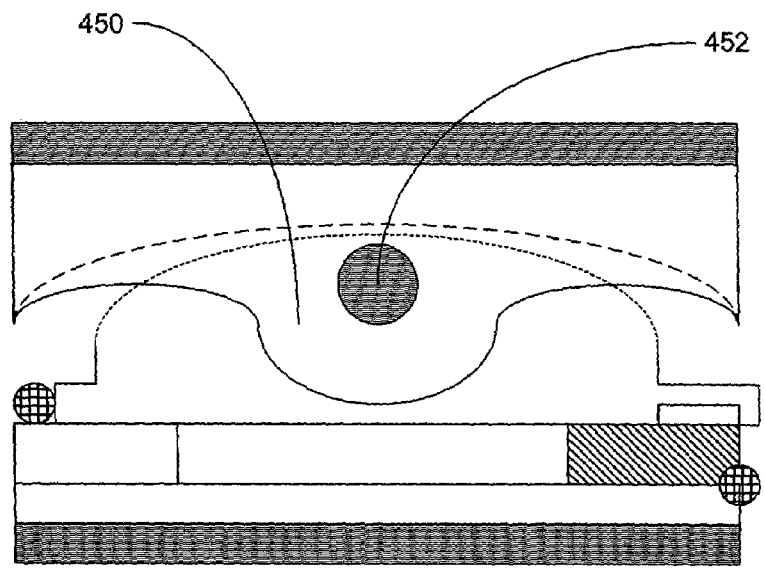
FIG. 14a is a lateral view of a banana-shaped lordotic expandable intervertebral implant prior to expansion.
Figure 14B:
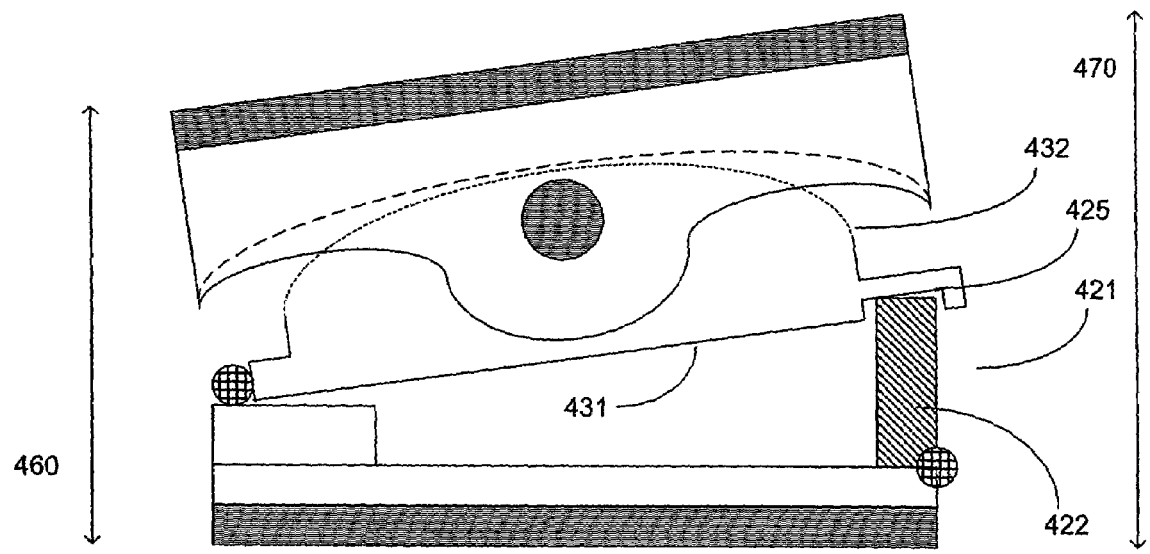
FIG. 14b is a lateral view of a banana-shaped lordotic expandable intervertebral implant following expansion.

Upper body 412 has a substantially concave inferior surface 416 that articulates with the substantially convex superior surface 432 of upper portion 430 of lower hinged body 414. When viewed in the medial or lateral direction, as shown in FIGS. 14*a* and 14*b*, upper body 412 has a downwardly projecting lobe 450 for the attachment of safety bar 452. Safety bar 452 secures upper body 412 to upper portion 430 of lower hinged body 414 and minimizes the possibility of dislocation.

Figure 13B:
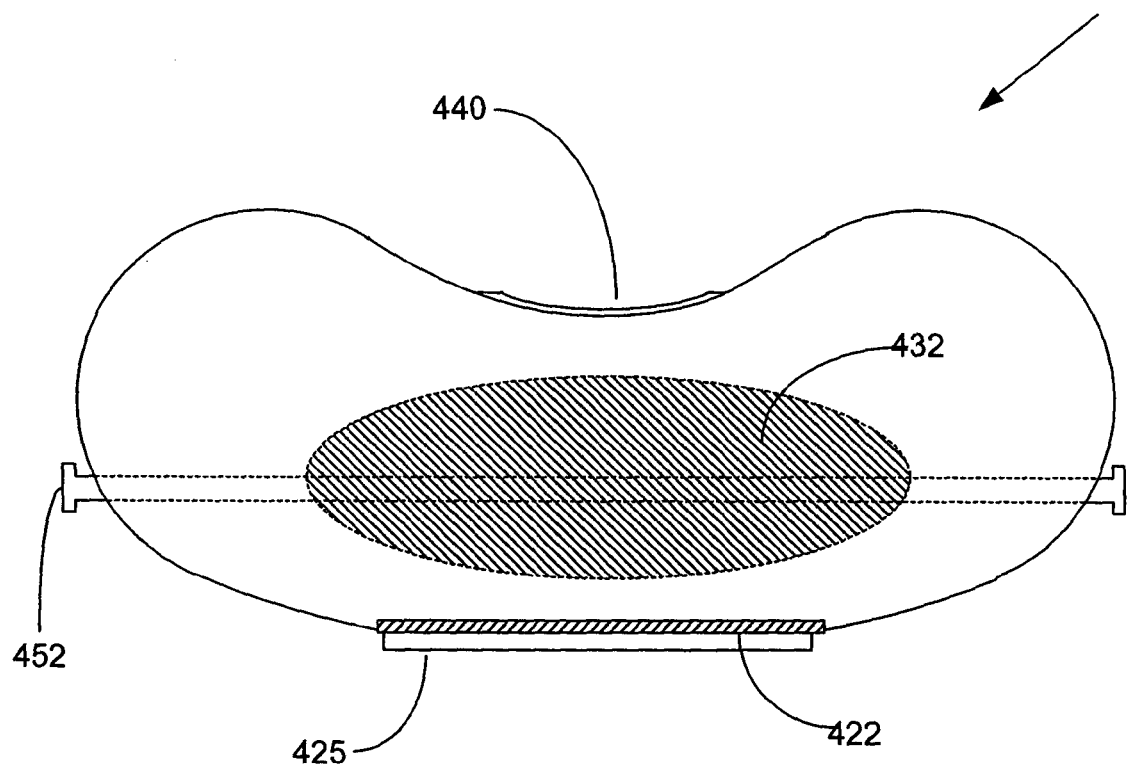
FIG. 13b is a top view of a banana-shaped lordotic expandable intervertebral implant.

FIG. 13*b* is a top view of lordotic expandable artificial intervertebral implant 400 illustrating the placement of posterior hinge 440, rotational lifting mechanism 422, and safety bar 452 affixed through upper body 412 and upper portion 430 of lower hinged body 414.

Figure 15A:
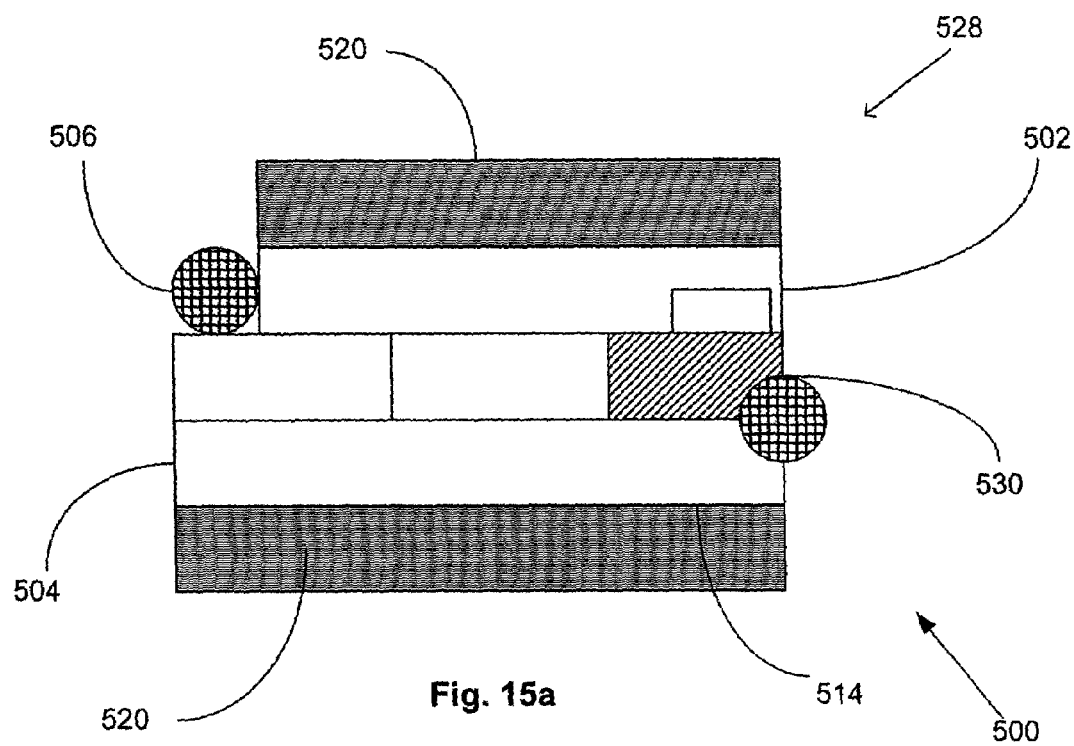
FIG. 15a is a side cross-sectional view of an expandable lordotic cage prior to expansion.
Figure 15B:
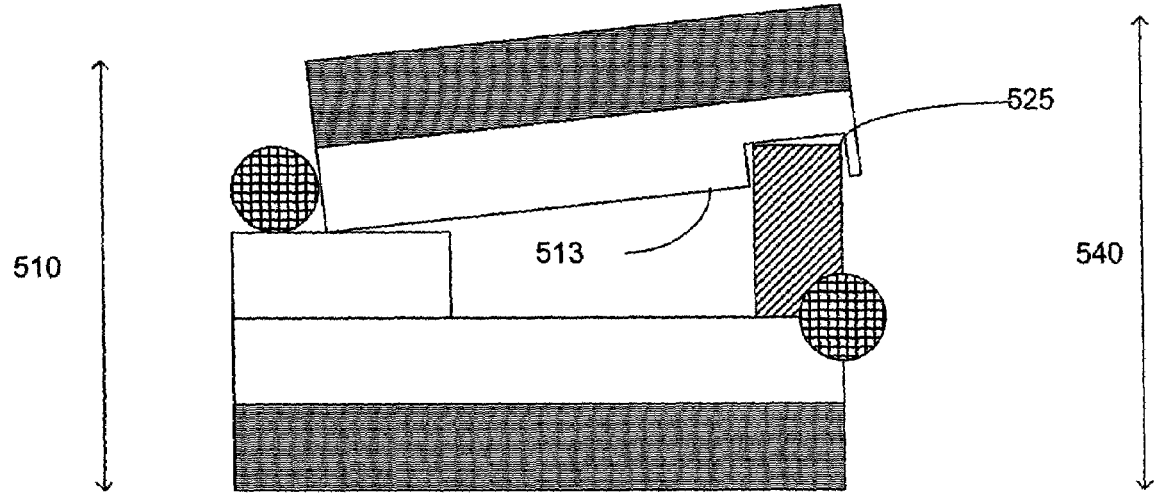
FIG. 15b is a side cross-sectional view of an expandable lordotic cage following expansion.

The rotational lifting mechanism described above may also be employed to achieve proper lordosis with an expandable PLIF and TLIF cage, as shown in FIGS. 15*a* and 15*b*. Cage 500 is shown prior to expansion in FIG. 15*a* and expanded in FIG. 15*b*. Cage 500 comprises an upper body 502 and a lower body 504. Hinge 506 posteriorly connects upper body 502 to lower body 504 and effectively fixes posterior disc height 510 upon expansion of cage 500. The superior surface 512 of upper body 502 and the inferior surface 514 of lower body 504 may include an osteoconductive scaffolding or mesh 520 as previously described. Expansion of cage 500 is accomplished via rotational lifting mechanism 530, which engages with securing notch 525, located on the anterior end 528 of the inferior surface 513 of upper body 502, and minimizes the potential for dislocation. The height of rotational lifting mechanism 530, which effectively fixes anterior disc height 540, is determined by the desired proper lordosis.

Figure 16A:
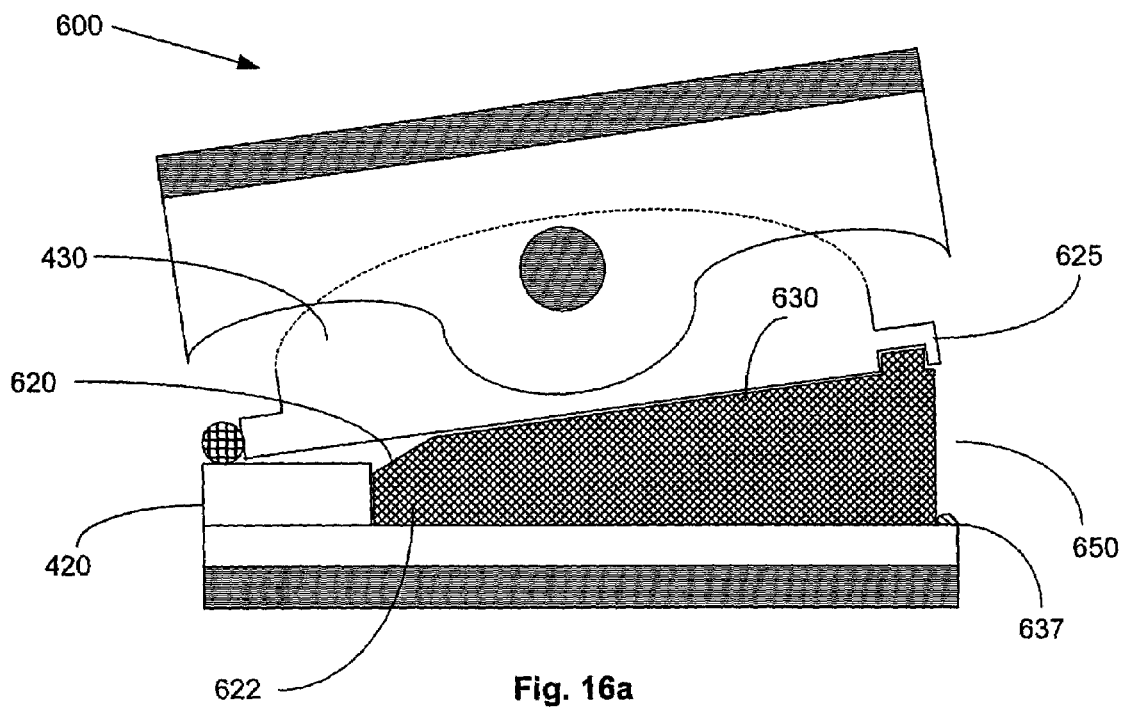
FIG. 16a is a lateral view of a banana-shaped lordotic expandable intervertebral implant featuring an inclined expansion plate.
Figure 16B:
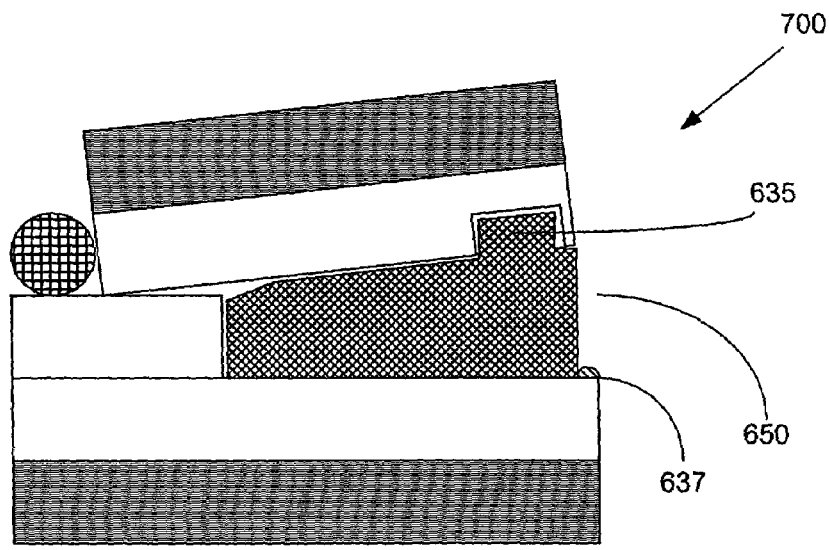
FIG. 16b is a side cross-sectional view of an expandable lordotic cage featuring an inclined expansion plate.

Another preferred embodiment of an expandable lordotic artificial intervertebral implant is illustrated in FIGS. 16*a* and 16*b*. Lordotic expandable intervertebral implant 600 and lordotic cage 700 both utilize an inclined expansion plate 650 to achieve proper lordosis. Both devices are similar to those described above with the exception of the expansion device and reference is made to FIGS. 14*a* and 14*b* for lordotic expandable intervertebral implant 600 and FIGS. 15*a* and 15*b* for lordotic cage 700 for elements of the intervertebral implants already identified. Expansion plate 650 is generally wedged-shaped and comprises a lifting notch 620 on its posterior end 622 to facilitate expansion. As shown in FIG. 16*a*, expansion plate 650 is installed between the upper portion 430 and lower portion 420 of lower hinged body 414. Located on the superior surface 630 at the anterior end 624 is securing ridge 635. Securing ridge 635 engages with securing notch 625 similar to the rotational lifting mechanism described above. Located on the anterior superior surface of lower portion 420 of lower hinged body 414 is a locking lip 637, which minimizes the potential of dislocating inclined expansion plate 650. FIG. 16*b* illustrate the use of expansion plate 650 in conjunction with lordotic cage 700.

Figure 17B:
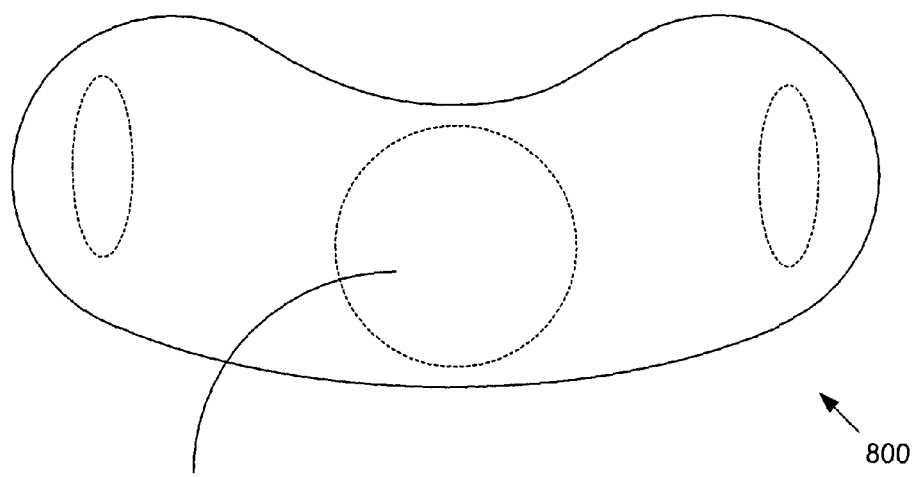
FIG. 17b is a side cross-sectional view of a banana-shaped intervertebral implant featuring an expansions plate and set screw prior to expansion.
Figure 17B:
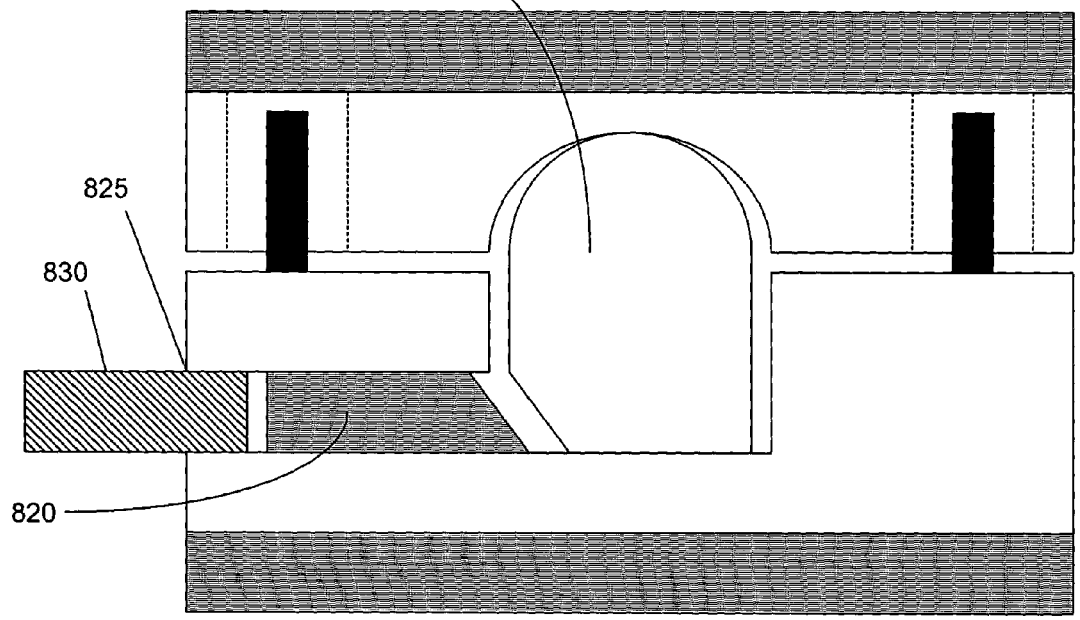
Figure 17C:
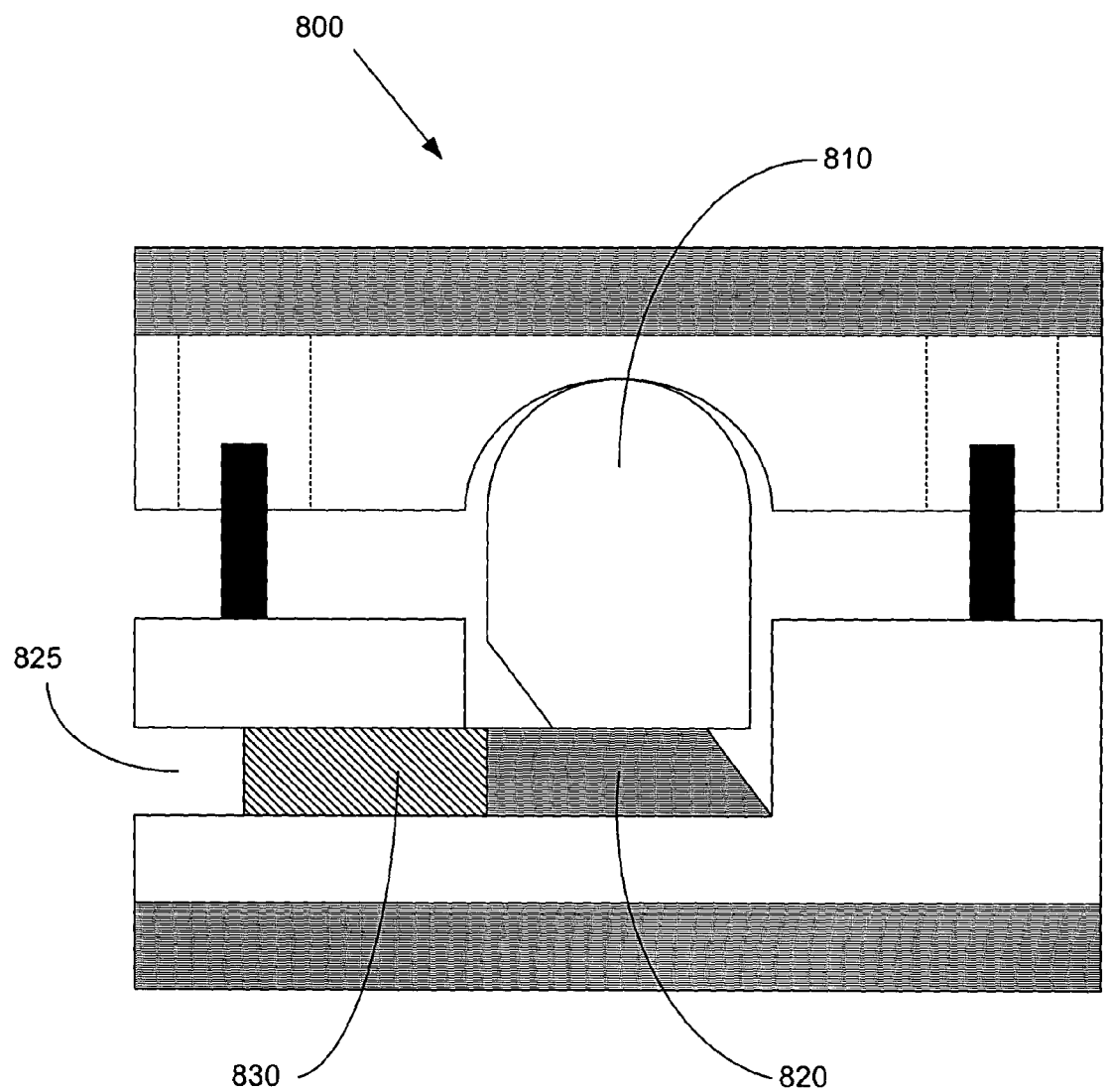
FIG. 17c is a side cross-sectional view of a banana-shaped intervertebral implant featuring an expansions plate and set screw following expansion.

FIGS. 17*a*, 17*b*, and 17*c* illustrate another preferred embodiment of the present invention. A banana-shaped expandable intervertebral implant 800 having a round joint insert 810 is shown in FIG. 17*a*. The round joint insert 810 provides the closest approximation to natural biomechanical motion. The side cross-sectional views of FIGS. 17*b* and 17*c* illustrate another preferred embodiment of an expansion device. Expansion plate 820 is inserted through expansion window 825 and is followed by the insertion of set screw 830. Expansion window 825 is threaded, which allows set screw 830 to advance expansion plate 820 into position below joint insert 810 as set screw 830 is screwed into expansion window 825. Set screw 830 prevents the dislocation of expansion plate 820 and allows the proper placement of expansion plate 820 with minimal impaction, which minimizes the stress on the surrounding area during the surgical procedure placing and expanding the device 800 in the intervertebral space. It should be noted that the expansion plate 820 and set screw 830 combination may be employed with any of the disclosed implants, including PLIF and TILF cages.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. An intervertebral implant for a human spine, comprising:
    an upper body comprising an inferior surface and a superior surface, wherein the superior surface of the upper body is configured to engage a first vertebra of the human spine;
    a lower body comprising a superior surface and an inferior surface, wherein the inferior surface of the lower body is configured to engage a second vertebra of the human spine;
    an insert comprising a superior surface and an inferior surface, wherein the insert is configured to be positioned between the superior surface of the lower body and the inferior surface of the upper body before insertion of the intervertebral implant between the first vertebra and the second vertebra of the human spine;
    an expansion member configured to engage the insert;
    a set screw configured to be rotated to advance the expansion member to engage the insert such that the insert increases a separation distance between the upper body and the lower body after insertion of the intervertebral implant in the human spine; and
    wherein the intervertebral implant is configured such that increasing the separation distance between the upper body and the lower body allows articulation or increased articulation of the intervertebral implant.

2. The intervertebral implant of claim 1, wherein the insert is configured to interact with at least a portion of the upper body or at least a portion of the lower body to increase the separation distance between the upper body and the lower body.

3. The intervertebral implant of claim 1, wherein at least a portion of the superior surface of the insert is convex, wherein at least a portion of the inferior surface of the upper body is concave, and wherein the concave portion of the inferior surface of the upper body is configured to be coupled to the convex portion of the superior surface of the upper body to allow articulation of the upper body with respect to the lower body during use.

4. The intervertebral implant of claim 1, wherein the insert comprises an angled portion, wherein the expansion member comprises an angled portion, and wherein the angled portion of the expansion member is configured to engage the angled portion of the insert to elevate the insert.

5. The intervertebral implant of claim 1, wherein the expansion member comprises a superior surface and an inferior surface, and wherein the superior surface and the inferior surface of the expansion member are substantially flat.

6. The intervertebral implant of claim 1, wherein advancing the expansion member comprises advancing the expansion member between the superior surface of the lower body and the inferior surface of the insert.

7. An intervertebral implant for a human spine, comprising:
    an upper body comprising an inferior surface and a superior surface, wherein the superior surface of the upper body is configured to engage a first vertebra of the human spine;
    a lower body comprising a superior surface and an inferior surface, wherein the inferior surface of the lower body is configured to engage a second vertebra of the human spine;
    an insert comprising a superior surface and an inferior surface, wherein the insert is configured to be positioned between the superior surface of the lower body and the inferior surface of the upper body such that the upper body contacts the lower body before insertion of the intervertebral implant between the first vertebra and the second vertebra of the human spine;
    an expansion member configured to engage the insert;
    a set screw configured to be rotated to advance the expansion member to engage the insert such that the insert increases a separation distance between the upper body and the lower body after insertion of the intervertebral implant in the human spine, wherein the set screw is configured to inhibit backout of the expansion member and maintain at least a portion of the increased separation distance between the upper body and the lower body during use; and
    wherein the intervertebral implant is configured such that increasing the separation distance between the upper body and the lower body allows articulation or increased articulation of the intervertebral implant.

8. The intervertebral implant of claim 7, wherein the insert is configured to interact with at least a portion of the upper body or at least a portion of the lower body to increase the separation distance between the upper body and the lower body.

9. The intervertebral implant of claim 7, wherein at least a portion of the superior surface of the insert is convex, wherein at least a portion of the inferior surface of the upper body is concave, and wherein the concave portion of the inferior surface of the upper body is configured to be coupled to the convex portion of the superior surface of the upper body to allow articulation of the upper body with respect to the lower body during use.

10. The intervertebral implant of claim 7, wherein the inferior surface of the insert is substantially flat, wherein the superior surface of the lower body comprises a recess, and wherein the inferior surface of the insert is configured to be positioned in the recess of the lower body.

11. The intervertebral implant of claim 7, wherein the insert comprises an angled portion, wherein the expansion member comprises an angled portion, and wherein the angled portion of the expansion member is configured to engage the angled portion of the insert to elevate the insert.

12. The intervertebral implant of claim 7, wherein the expansion member comprises a superior surface and an inferior surface, and wherein the superior surface and the inferior surface of the expansion member are substantially flat.

13. The intervertebral implant of claim 7, wherein advancing the expansion member comprises advancing the expansion member between the superior surface of the lower body and the inferior surface of the insert.

14. An intervertebral implant for a human spine, comprising:
   an upper body comprising an inferior surface and a superior surface, wherein the superior surface of the upper body is configured to engage a first vertebra of the human spine, and wherein at least a portion of the inferior surface is concave;
   a lower body comprising a superior surface and an inferior surface, wherein the inferior surface of the lower body is configured to engage a second vertebra of the human spine, and wherein the superior surface of the lower body comprises a recess;
   an insert comprising a superior surface and an inferior surface, wherein at least a portion of the superior surface of the insert is convex, wherein the inferior surface of the insert is substantially flat, and wherein the insert is configured to be positioned such that the inferior surface of the insert is positioned in the recess in the superior surface of the lower body and the convex portion of the superior surface of the insert is coupled to the concave portion of the inferior surface of the upper body before insertion of the intervertebral implant between the first vertebra and the second vertebra of the human spine;
   an expansion member configured to engage the insert; and
   a set screw positioned in an opening in a short end or a long side of the lower body, wherein the set screw is configured to be rotated to advance the expansion member to engage the insert such that the insert increases a separation distance between the upper body and the lower body after insertion of the intervertebral implant in the human spine.

15. The intervertebral implant of claim 14, wherein the insert is configured to interact with at least a portion of the upper body or at least a portion of the lower body to increase the separation distance between the upper body and the lower body.

16. The intervertebral implant of claim 14, wherein the concave portion of the upper body and the convex portion of the insert are coupled to allow articulation of the upper body with respect to the lower body during use.

17. The intervertebral implant of claim 14, wherein the insert comprises an angled portion, wherein the expansion member comprises an angled portion, and wherein the angled portion of the expansion member is configured to engage the angled portion of the insert to elevate the insert.

18. The intervertebral implant of claim 14, wherein the expansion member comprises a superior surface and an inferior surface, and wherein the superior surface and the inferior surface of the expansion member are substantially flat.

19. The intervertebral implant of claim 14, wherein advancing the expansion member comprises advancing the expansion member between the superior surface of the lower body and the inferior surface of the insert.

20. The intervertebral implant of claim 14, wherein increasing the separation distance between the upper body and the lower body allows articulation or increased articulation of the intervertebral implant.

* * * * *